(12) United States Patent
Ober et al.

(10) Patent No.: US 8,192,843 B2
(45) Date of Patent: Jun. 5, 2012

(54) POLYMERS AND POLYMER COATINGS

(75) Inventors: Christopher K. Ober, Ithaca, NY (US); Sitaraman Krishnan, Ithaca, NY (US); Qin Lin, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 13/026,615

(22) Filed: Feb. 14, 2011

(65) Prior Publication Data
US 2011/0177343 A1 Jul. 21, 2011

Related U.S. Application Data

(60) Division of application No. 11/507,355, filed on Aug. 21, 2006, now Pat. No. 7,887,790, which is a continuation-in-part of application No. 11/063,242, filed on Feb. 22, 2005, now Pat. No. 7,709,055.

(60) Provisional application No. 60/709,925, filed on Aug. 19, 2005, provisional application No. 60/546,656, filed on Feb. 20, 2004.

(51) Int. Cl.
*B32B 27/30* (2006.01)
*C08F 293/00* (2006.01)
*C09D 5/16* (2006.01)

(52) U.S. Cl. .................. 428/421; 523/122; 525/276

(58) Field of Classification Search .................. None
See application file for complete search history.

(56) References Cited

U.S. PATENT DOCUMENTS

| | | | |
|---|---|---|---|
| 4,011,178 A | 3/1977 | Muse | |
| 4,480,075 A | 10/1984 | Willis | |
| 4,659,785 A | 4/1987 | Nagano et al. | |
| 5,336,717 A | 8/1994 | Rolando et al. | |
| 5,725,789 A * | 3/1998 | Huber et al. | 252/8.62 |
| 5,907,017 A | 5/1999 | Ober et al. | |
| 6,114,467 A | 9/2000 | Ober et al. | |
| 6,583,228 B2 | 6/2003 | Nkansah et al. | |
| 6,750,296 B2 | 6/2004 | Ober et al. | |
| 7,709,055 B2 | 5/2010 | Ober et al. | |
| 7,763,687 B2 | 7/2010 | Ober et al. | |

(Continued)

FOREIGN PATENT DOCUMENTS

DE 19910811 9/2000

(Continued)

OTHER PUBLICATIONS

Krishnan et al., Anti-Biofouling Properties of Comblike Block Copolymers with Amphiphilic Side Chains, Apr. 2006, Langmuir, vol. 22, pp. 5075-5086.*

(Continued)

*Primary Examiner* — Callie Shosho
*Assistant Examiner* — Patrick English
(74) *Attorney, Agent, or Firm* — Schwegman, Lundberg Woessner, P.A.

(57) ABSTRACT

The invention provides polymers, methods of preparing polymers, and compositions that include polymers, wherein said polymers include a plurality of two-carbon repeating units in a polymer chain, wherein one or more of the two-carbon repeating units of the polymer chain have a substituent that is covalently bonded to a semifluorinated alkyl ethoxy moiety, and the semifluorinated alkyl ethoxy moiety is attached to the polymer chain substituent through an ester, amide, ketone, carbamate, amine, or other suitable linking group. The polymers can be used to provide antifouling coatings.

8 Claims, 6 Drawing Sheets

U.S. PATENT DOCUMENTS

| | | | |
|---|---|---|---|
| 7,887,790 | B2 | 2/2011 | Ober |
| 2006/0083854 | A1 | 4/2006 | Ober et al. |
| 2007/0053867 | A1 | 3/2007 | Ober et al. |
| 2007/0106040 | A1 | 5/2007 | Ober et al. |
| 2010/0280201 | A1 | 11/2010 | Ober et al. |

FOREIGN PATENT DOCUMENTS

| | | |
|---|---|---|
| EP | 0337474 | 10/1989 |
| JP | 2002105152 | 4/2002 |

OTHER PUBLICATIONS

"U.S. Appl. No. 11/063,242 Notice of Allowance Mailed Dec. 14, 2009", 8.

"U.S. Appl. No. 11/063,242, Response filed Nov. 19, 2008 to Non-Final Office Action mailed Aug. 19, 2008", 13 pgs.

"U.S. Appl. No. 11/063,242, Non-Final Office Action mailed Aug. 19, 2008", 8 pgs.

"U.S. Appl. No. 11/063,242, Supplemental Amendment and Response filed Jan. 14, 2009 to Notice of Non-Compliant mailed Dec. 22, 2008", 10.

"U.S. Appl. No. 11/063,242, Non-Final Office Action mailed Apr. 1, 2009", 8 pgs.

"U.S. Appl. No. 11/063,242, Response filed Jul. 1, 2009 to Non Final Office Action mailed Apr. 1, 2009", 13 pgs.

"U.S. Appl. No. 11/507,355 Notice of Allowance mailed Oct. 5, 2010", 8 pgs.

"U.S. Appl. No. 11/507,355, Restriction Requirement mailed Apr. 23, 2009", 5 pgs.

"U.S. Appl. No. 11/507,355, Non-Final Office Action mailed May 6, 2010", 7 pgs.

"U.S. Appl. No. 11/507,355, Non-Final Office Action mailed Aug. 4, 2009", 14 pgs.

"U.S. Appl. No. 11/507,355, Response filed Dec. 31, 2009 to Non Final Office Action mailed Aug. 4, 2009", 13 pgs.

"U.S. Appl. No. 11/507,355, Response filed May 26, 2009 to Restriction Requirement mailed", 9 pgs.

"U.S. Appl. No. 11/507,355, Response filed Aug. 6, 2010 to Non Final Office Action mailed May 6, 2010", 27 pgs.

"U.S. Appl. No. 11/507,361, Non-Final Office Action mailed Mar. 10, 2010", 10.

"U.S. Appl. No. 11/507,361, Non-Final Office Action mailed Jul. 30, 2009", 11 pgs.

"U.S. Appl. No. 11/507,361, Response filed Nov. 30, 2009 to Non Final Office Action mailed Jul. 30, 2009", 8 pgs.

"Barnacle Free Boats", ScienCentralNews, (Observed Feb. 28, 2005), 3 pgs.

"DuPont tm Zonyl (r) FSO—Fluorosurfactant", Dupont Technical Information Sheet (P-200125.8), (2002), 2 pgs.

"DuPont tm Zonyl (r) FSN—Fluorosurfactant", DuPont Technical Information Sheet (P-200125.8), (2002), 2 pgs.

"DuPont tm Zonyl (r) FSN-100—Fluorosurfactant", DuPont Technical Information Sheet (P-200125.8), (2002), 2 pgs.

"DuPont tm Zonyl (r) FSO-100—Fluorosurfactant", DuPont Technical Information Sheet (P-200125.8), (2002), 2 pgs.

Baier, R. E., "Influence of the Initial Surface Condition of Materials on Bioadhesion", (Published Prior to Sep. 22, 2005), 633-639.

Callow, M. E., et al., "Microtopographic Cues for Settlement of Zoospores of the Green Fouling Alga *Enteromorpha*", Biofouling, 18(3), (2002), 237-245.

Callow, M. E., et al., "Primary Adhesion of *Enteromorpha* (Chlorophyta, Ulvales) Progagules: Quantitative Settlement Studies and Video Microscopy", J. Phycol., 33, (1997), 938-947.

Callow, M. E., et al., "The Influence of Low Surface Energy Materials on Bioadhesion—a Review", International Biodeterioration & Biodegradation, (1994), 333-348.

Callow, M. E., et al., "Use of Self-Assembled Monolayers of Different Wettabilities to Study Surface Selection and Primary Adhesion Processes of Green Algal (*Enteromorpha*) Zoospores", Applied and Environmental Microbiology, 66(8), (2000), 3249-3254.

Chapman, Toby M, et al., "Determination of Low Critical Surface Tensions of Novel Fluorinated Poly(amide urethane) Block Copolymers. 1. Fluorinated Side Chains", Macromolecules, vol. 28, No. 1, (1995), 331-335.

Chapman, Toby M, et al., "Determination of Low Critical Surface Tensions of Novel Fluorinated Poly(amide urethane) Block Copolymers. 2. Fluorinated Soft-Block Backbone and Side Chains", Macromolecules, vol. 28, No. 6, (1995), 2081-2085.

Cormack, P., et al., "Molecular imprinting: recent developments and the road ahead", Reactive and Functional Polymers, 41(1-3), (Jul. 15, 1999), 115-124.

Davis, K. A., "ABC Triblock Copolymers Prepared Using Atom Transfer Radical Polymerization Techniques", Macromolecules, 34(7), (2001), 2101-2107.

Fields, S., et al., "New Paint: No Harm, No Foul?", Environmental Health Perspectives, 111(9), (2003), A457.

Finlay, J. A., et al., "Adhesion Strength of Settled Spores of the Green Alga *Enteromorpha*", Biofouling, 18(4), (2002), 251-256.

Finlay, J. A., et al., "The Influence of Surface Wettability on the Adhesion Strength of Settled Spores of the Green Alga *Enteromorpha* and the Diatom Amphora", Integr. Comp. Biol., 42, (2002), 1116-1122.

Freij-Larsson, C., et al., "Adsorption Behaviour of Amphiphilic Polymers at Hydrophobic Surfaces: Effects on Protein Adsorption", Biomaterials, 17(22), (Nov. 1996), 2199-2207.

Gudipati, C. S., et al., "The Antifouling and Fouling-Release Performance of Hyperbranched Fluoropolymer (HBFP)-Poly(ethylene glycol)(PEG) Composite Coatings Evaluated by Adsorption of Biomacromolecules and the Green Fouling Alga Ulva", Langmuir, 21(7), (2005), 3044-3053.

Hexemer, A., et al., "Managing Polymer Surface Structure Using Surface Active Block Copolymers in Block Copolymer Mixtures", Journal of Polymer Science Part B: Polymer Physics, 42(3), (2003), 411-420.

Hourdet, D., et al., "Synthesis of Thermoassociative Copolymers", Polymer, 38(10), (May 1997), 2535-2547.

Hussain, H., et al., "Amphiphilic Block Copolymers of Poly(ethylene oxide) and Poly(perfluorohexylethyl methacrylate) at the Water Surface and Their Penetration into the Lipid Monolayer", J. Phys. Chem. B., 108(28), (2004), 9962-9969.

Kang, Seok Ho, et al., "Synthesis and Characterization of Diblock Copolymers Containing Surface Modifying Moieties for Non-Biofouling Materials", Polymer Preprints, vol. 41, No. 2, (Aug. 2000), 1521-1522.

Keszler, B., et al., "Amphiphilic Networks—V. Polar/Nonpolar Surface Characteristics, Protein Adsorption From Human Plasma and Cell Adhesion", Polymer Bulletin, 29, (1992), 681-688.

Kobayashi, Hideki, et al., "Surface Properties of Fluorosilicones", Trends in Polymer Science, vol. 3, No. 10, (Oct. 1995), 330-335.

Krishnan, S., et al., "Anti-Biofouling Properties of Comblike Block Copolymers With Amphiphilic Side Chains", Langmuir, 22, (2006), 5075-5086.

Krishnan, S., et al., "Antibacterial Coatings Based on Quaternized Poly(4-vinylpyridine) Block Copolymers", PMSE Preprints, 91, (2004), 814-815.

Krishnan, S., et al., "Comparison of the Fouling Release Properties of Hydrophobic Fluorinated and Hydrophilic PEGylated Block Copolymer Surfaces: Attachment Strength of the Diatom Navicula and the Green Alga Ulva", Biomacromolecules, 7, (2006), 1449-1462.

Lee, S. B., et al., "Permanent, Nonleaching Antibacterial Surfaces. 1. Synthesis by Atom Transfer Radical Polymerization", Biomacromolecules, 5, (2004), 877-882.

Li, J., et al., "Synthesis of Polyethylene Glycol (PEG) Derivatives and PEGylated-Peptide Biopolymer Conjugates", Biomacromolecules, 4(4), (2003), 1055-1067.

Mao, G., et al., "Molecular Design, Synthesis, and Characterization of Liquid Crystal-Coil Diblock Copolymers with Azobenzene Side Groups", Macromolecules, 30, (1997), 2556-2567.

Masson, P., et al., "Thermotropic Liquid Crystalline Behaviour of Pyridinium and Poly(4-vinylpyridinium) Salts Quaternized With w-alkyl Phenylbenzoate Derivatives", Macromolecular Chemistry and Physics, 200(3), (1999), 616-620.

Ober, et al., "Block copolymers as surface modifiers: Synthesis, characterization and relevance to fouling release and biostability", PMSE Preprints, 88, (2003), 612-613.

Ober, C. K., "Non-Leaching, Benign, Fouling Control, Multilayer Polymer Coatings for Marine Applications: pp. 1274 Findings", Report submitted to The Strategic Enviironmental Research and Development Program (SERDP), (2003), 21 pgs.

Ober, C. K., et al., "Surface-Active Materials With Antifouling Properties", ACS 2004 Presentation, (2004), 29 pgs.

Ober, C. K., et al., "Surface-Active Materials With Antifouling Properties", Polymer Preprints, 45(1), (2004), 2 pgs.

Ostuni, E., et al., "Self-Assembled Monolayers That Resist the Adsorption of Proteins and the Adhesion of Bacterial and Mammalian Cells", Langmuir, 17, (2001), 6336-6343.

Park, D., et al., "Amphiphilic Networks. 9. Surface Characterization", Macromolecules, 28(8), (1995), 2595-2601.

Pike, John K, et al., "Time-Dependent Dynamic Contact Angle Analysis of Poly(dimethylsiloxane-urethane-urea) Segmented Block Copolymer Films", Polymer Preprints, vol. 36, No. 2, (1995), 67-68.

Pike, John K, et al., "Water-Induced Surface Rearrangements of Poly(dimethylsiloxane-urea-urethane) Segmented Block Copolymers", Chemistry of Materials, vol. 8, No. 4, (Apr. 1996), 856-860.

Poe, G. D., et al., "Enhanced Coil Expansion and Intrapolymer Complex Formation of Linear Poly(methacrylic acid) Containing Poly(ethylene glycol) Grafts", Macromolecules, 37(7), (2004), 2603-2612.

Sigal, G. B., et al., "Effect of Surface Wettability on the Adsorption of Proteins and Detergents", J. Am. Chem. Soc., 120, (1998), 3464-3473.

Swain, G. W., et al., "The Influence of Biofouling: Adhesion and Biotic Distrubance on the Development of Fouling Communities on Non-Toxic Surfaces", Biofouling, 12(1-3), (1998), 257-269.

Tiller, J. C., et al., "Designing Surfaces That Kill Bacteria on Contact", Proc. Natl. Acad. Sci. USA, 98(11), (May 22, 2001), 5981-5985.

Vreeland, V., et al., "Polyphenols and Oxidases in Substratum Adhesion by Marine Algae and Mussels", J. Phycol., 34, (1998), 1-8.

Wang, J., "Liquid Crystalline, Semifluorinated Side Group Block Copolymers with Stable Low Energy Surfaces: Synthesis, Liquid Crystalline Structure, and Critical Surface Tension", Macromolecules, 30(7), (Apr. 1997), 1906-1914.

Wang, J., et al., "Self-Organizing Materials With Low Surface Energy: The Synthesis and Solid-State Properties of Semifluorinated Side-Chain Ionenes", Macromolecules, 30(24), (1997), 7560-7567.

Wynne, K. J., et al., "Two Silicone Nontoxic Fouling Release Coatings: Hydrosilation Cured PDMS and CaCO3 Filled, Ethoxysiloxane Cured RTV11", Biofouling, 16(2-4), (2000), 277-288.

Xiang, Maoliang, "Surface Stability in Liquid-Crystalline Block Copolymers with Semifluorinated Monodendron Side Groups", Macromolecules, vol. 33, No. 16, (Aug. 2000), 6106-6119.

Youngblood, J. P., et al., "Coatings Based on Side-Chain Ether-Linked Poly(ethylene glycol) and Fluorocarbon Polymers for the Control of Marine Biofouling", Biofouling, 19 (Supplement), (2003), 91-98.

Zhu, J., et al., "Interfacial behavior of block polyelectrolytes. 6. Properties of surface micelles as a function of R and X in P(S260-b-VP240/RX)", Macromolecules, 25(24), (1992), 6556-62.

* cited by examiner

POLYMERS AND POLYMER COATINGS

RELATED APPLICATIONS

This application is a divisional of U.S. patent application Ser. No. 11/507,355, filed Aug. 21, 2006 now U.S. Pat. No. 7,887,790, issued on Feb. 15, 2011, which claims priority under 35 U.S.C. §119(e) to U.S. Provisional Patent Application No. 60/709,925, filed Aug. 19, 2005, and this application is also a continuation-in-part of U.S. patent application Ser. No. 11/063,242, filed Feb. 22, 2005, now U.S. Pat. No. 7,709, 055, which claims priority under 35 U.S.C. §119(e) to U.S. Provisional Patent Application No. 60/546,656, filed Feb. 20, 2004, which applications are incorporated herein by reference.

GOVERNMENT SUPPORT

This invention was made with Government support under Grant Numbers N00014-02-1-0170 awarded by the Office of Naval Research and PP-1454 awarded by the Strategic Environmental Research and Development Program (SERDP) of the Department of Defense. The United States Government has certain rights in this invention.

BACKGROUND OF THE INVENTION

Marine fouling is a major problem in the transport of materials by sea as it can raise fuel consumption by as much as 30%. Environmentally friendly coatings that protect the hulls of ships below the waterline against fouling by seaweed, barnacles, and other organisms are currently sought by the shipping industry. Fouling by these organisms produces additional drag on the ship, thereby increasing operating and maintenance costs.

Antifouling paints containing tin and copper biocides are currently used because of their effectiveness against most forms of marine fouling. Many of these biocidal organometallic compounds are environmentally persistent. They can cause damage to the ecosystem and enter the food chain. A total ban by the International Maritime Organization on the presence of tributyltin (TBT) antifoulants on vessel hulls will be effective in 2008, and copper-based coatings are expected to face similar restrictions in the near future.

Non-toxic "fouling-release" or "fouling-repellant" coatings are one class of alternatives to biocidal coatings. Silicone-based paints are commercially available, but do not satisfy many desired performance characteristics. The soft silicones do not withstand the rigorous demands of the marine environment, do not sufficiently and consistently self-clean, or, due to polymer restructuring or other degradation pathways, lose many of the desirable surface properties with time and exposure to marine organisms.

Several fouling release (FR) coating systems are commercially available, mostly based on silicone polymers, yet none meet all of the desired performance characteristics. Many commercially available coating systems lack the toughness required to withstand the rigorous physical demands of the marine environment, do not sufficiently and consistently self-clean, and due to polymer restructuring or other degradation pathways, lose many of the desirable surface properties with time and exposure to the marine environment.

Accordingly, what is needed is a material that lowers the strength of adhesion between fouling organisms and a surface, for example, a marine surface. What is also needed is a surface that is resistant to marine biofouling, for example, fouling by marine organisms such as zoospores and diatoms (unicellular algae). The diversity of fouling organisms and environmental conditions worldwide makes the task of developing a coating that resists fouling and/or self-cleans challenging, and novel non-toxic solutions to the problems of biofouling are urgently needed.

SUMMARY

The invention provides polymers, methods of preparing polymers, and compositions that include polymers, wherein said polymers include a plurality of two-carbon repeating units in a polymer chain, wherein one or more of the two-carbon repeating units of the polymer chain have a substituent that is covalently bonded to a moiety of formula Z:

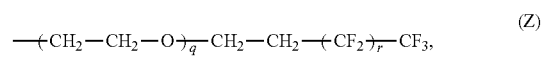

wherein q is independently 1 to about 25; r is independently 0 to about 18; and the moiety of formula Z is attached to the polymer chain substituent through an ester, amide, ketone, carbamate, or amine.

The polymer can include other types of chain substituents, for example, one or more polymer chain substituents selected from aryl groups, alkyl groups, and alkoxycarbonyl groups, wherein any alkyl, aryl, or alkoxy is optionally substituted with one or more alkyl, alkoxy, hydroxy, halo, dialkylamino, trifluoromethyl, ethylene glycol, or perfluoroalkyl groups. The two-carbon repeating units in the polymer chain can include polystyrene units, polyisoprene units, polybutadiene units, polyacrylate units, polymethacrylate units, or a combination thereof, among other types of polymer units.

The polymer chain substituent can be, for example, a carboxy group and the moiety of formula Z can be attached to the carboxy group to form an ester linkage.

The invention also provides a polymer that includes formula I:

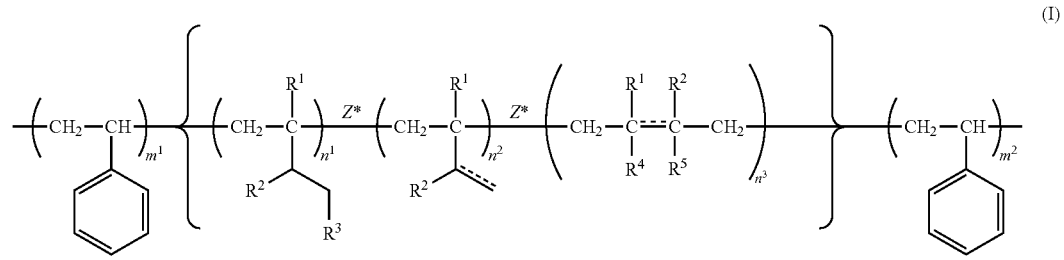

wherein $m^1$ is about 5 to about 2000;

$m^2$ is absent or is independently about 5 to about 2000;

$n^1$ is about 5 to about 2,000;

$n^2$ is absent or is independently about 5 to about 2000;

$n^3$ is absent or is independently about 5 to about 2000;

the dispersement of each individual $n^1$, $n^2$, and $n^3$ subunit on either side of either z* is random and each individual $n^1$, $n^2$, and $n^3$ subunit occurs interchangeably with any other $n^1$, $n^2$, or $n^3$ subunit within the brackets of formula I;

each $R^1$ is independently hydrogen or methyl and each $R^2$ is independently hydrogen or methyl provided that at least one of $R^1$ and $R^2$ within each n subunit is hydrogen;

each $R^3$ is independently H, OH, or halo; or alkyl wherein alkyl is optionally at least partially fluorinated; alkyl-terminated (-ethylene glycol-)$_n$ wherein n is about 2 to about 24; wherein each alkyl or alkyl-terminated (-ethylene glycol-)$_n$ is covalently bonded to the carbon of $R^3$ through an ester, amide, or amino group; or a moiety of formula Z:

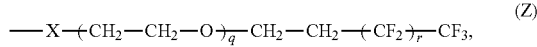

(Z)

wherein each X is independently —O—C(=O)—CH$_2$—O—, —NH—C(=O)—CH$_2$—O—, or —NH—, linking the moiety of formula Z to the carbon attached to $R^3$, each q is independently 1 to about 25, and each r is independently 1 to about 18;

provided that at least one $R^3$ of formula I is a moiety of formula Z;

each $R^4$ and $R^5$ is independently hydrogen, $R^3$, or absent, provided that when $R^4$ is hydrogen, $R^5$ is $R^3$; and when $R^4$ is $R^3$, $R^5$ is hydrogen; and each individual bond represented by — is an optional double bond, provided that when the bond between the carbons of $R^4$ and $R^5$ is present, $R^4$ and $R^5$ are absent.

In one embodiment, each X can be —O—C(=O)—CH$_2$—O—, q can be 1 to about 15, and r can be 0 to about 8.

The invention further provides a polymer that includes formula (II):

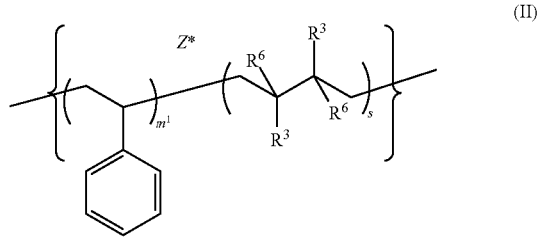

(II)

wherein $m^1$ is about 5 to about 2000;

s is about 5 to about 2000;

each $R^6$ is independently H or alkyl, provided that when one $R^6$ of any given subunit s is alkyl, the other $R^6$ of the same subunit s is H;

each $R^3$ is independently H, OH, halo, carboxy, or alkyl wherein alkyl is optionally at least partially fluorinated; alkyl-terminated (-ethylene glycol-)$_n$ wherein n is about 2 to about 24; wherein each alkyl or alkyl-terminated (-ethylene glycol-)$_n$ is covalently bonded to the carbon of $R^3$ through an ester, amide, or amino group; or a moiety of formula Z:

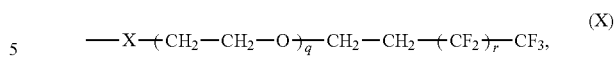

(X)

wherein each X is independently —C(=O)—O— or —C(=O)—NH—, linking the moiety of formula Z to the carbon attached to $R^3$, each q is independently 1 to about 25, and each r is independently 1 to about 18;

provided that when one $R^3$ of any given subunit s is a moiety of formula Z, the other $R^3$ of the same subunit s is not a moiety of formula Z;

provided that at least one $R^3$ of formula II is a moiety of formula Z; and the dispersement of each individual s subunit and each individual $m^1$ subunit on either side of z* is random and each individual s subunit and each individual $m^1$ subunit occurs interchangeably with any other s or $m^1$ subunit within the brackets of formula II.

In one embodiment, each X can be —C(=O)—O—, q can be 1 to about 15, and r can be 0 to about 8.

The polymer can be a random polymer, or alternatively, a block copolymer, depending on the process used to prepare the polymer. The polymer can have a molecular weight of about 5 kDa to about 2,000 kDa.

The moiety of formula Z can include values of q and r wherein each q is 1 to about 15 and each r is 0 to about 8.

The polymer can exhibit antifouling properties toward one or more of marine algae, algal spores, bacterial cells, diatoms, and protozoa.

The invention also provides an antifouling surface that includes a surface coating that includes a polymer as described above. The antifouling surface can optionally include a base layer. The base layer can be, for example, an elastomeric polymer.

DETAILED DESCRIPTION

Figure 1:
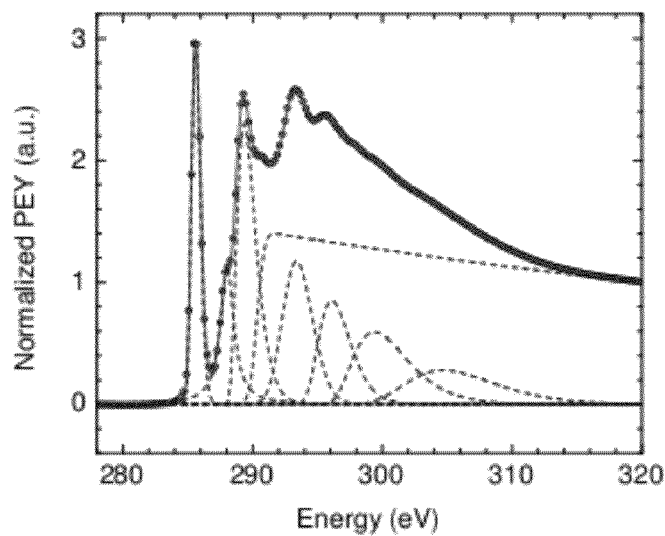
FIG. 1 illustrates a NEXAFS spectrum of a spin-coated surface of amphiphilic polymer on a silicon wafer after annealing at 120° C. for 12 hours; circles are experimental data points, the solid line is the best-fit curve, and the curves with dotted lines are deconvoluted peaks.

Marine surfaces have a tendency to rapidly accumulate colonizing organisms that may range from microscopic bacteria, cyanobacteria, spores of algae and unicellular eukaryotes such as diatoms, to larger larvae of invertebrates. Colonization starts within minutes to hours of immersion of the surface in water, which is followed by the formation of a biofilm consisting of firmly attached cells. Attached algal spores or invertebrate larvae rapidly grow into macroscopic adults. Accumulation of biomass on a ship hull due to the above process is undesirable from the point of view of higher hydrodynamic drag resulting in lower operational speeds or increased fuel consumption.

Certain toxic paints used to prevent biofouling have raised environmental concerns. Bio-accumulating metals in the paints can leach into marine environments, adversely affecting the marine ecosystem. A more environmentally friendly approach is to use non-toxic coatings that can resist colonization by fouling organisms or minimize the strength of adhesion of those organisms that do attach and grow on the surface. Both settlement and adhesion of marine cells are affected by chemical, topographic, and biological cues, and can vary from one species to another.

It is now known that although settlement of the zoospores is strongly promoted by a hydrophobic poly(dimethyl siloxane) (PDMS) surface, attachment strength of both the spores and sporelings is significantly weaker than on a hydrophilic glass substrate. This is a favorable aspect from the standpoint of currently used PDMS antifouling coatings. PDMS elastomers are widely used in commercial foul-release coatings due to their combination of properties such as low surface-energy, low microroughness and low modulus. *Ulva* sporelings release readily from PDMS.

In contrast, diatoms (unicellular algae) show strong adhesion to PDMS and it is well know that marine biofilms dominated by diatoms do not release easily from PDMS-based fouling-release coatings. A key challenge of marine antifouling research, therefore, is to find a surface that is resistant to fouling by both organisms.

The following definitions are used, unless otherwise described. Specific values listed below for radicals, substituents, and ranges, are for illustration only; they do not exclude other defined values or other values within defined ranges for the radicals and substituents. The term "about" refers to a value that is greater than or less than the specified value by 5%, 10%, or 25%. The term "about" can also refer to a value that is greater than or less than the specified value by one or two integers.

The phrase "one or more" is readily understood by one of skill in the art, particularly when read in context of its usage. For example, one or more substituents on a phenyl ring refers to one to five, or one to four, for example if the phenyl ring is disubstituted. One or more subunits of a polymer can refer to about 5 to about 50,000, or any increment of about 100 or about 1,000 within that range. In other embodiments, one or more refers to 1 to about 50, 1 to about 30, 1 to about 20, 1 to about 12, 1 to about 10, 1 to about 8, 1 to about 5, 1 to about 3, or 2.

It will be appreciated by those skilled in the art that compounds or polymers of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by synthesis from optically-active starting materials, by using resolution of the racemic form by recrystallization techniques, by chiral synthesis, or by chromatographic separation using a chiral stationary phase). Thus, the compounds and polymers of this invention include all stereochemical isomers arising from the various structural variations of these compounds.

References in the specification to "one embodiment", "an embodiment", "an example embodiment", etc., indicate that the embodiment described may include a particular feature, structure, or characteristic, but every embodiment may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

"Substituted" is intended to indicate that one or more hydrogens on a group indicated in the expression using "substituted" is replaced with a selection from the indicated group(s), provided that the indicated atom's normal valency is not exceeded, and that the substitution results in a stable compound. Suitable indicated groups include, e.g., alkyl, alkenyl, alkylidenyl, alkenylidenyl, alkoxy, aryloxy, halo, haloalkyl, hydroxy, hydroxyalkyl, aryl, heteroaryl, heterocycle, cycloalkyl, alkanoyl, alkoxycarbonyl, aroyl, acyloxy, aroyloxy, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, ethylene glycol, isocyannato, sulfamoyl, sulfinamoyl, sulfino, sulfo, sulfoamino, thiosulfo, $NR^xR^y$ and/or COM', wherein each $R^x$ and $R^y$ are independently H, alkyl, alkenyl, aryl, heteroaryl, heterocycle, cycloalkyl or hydroxy. As would be readily understood by one skilled in the art, when a substituent is keto (i.e., =O) or thioxo (i.e., =S), or the like, then two hydrogen atoms on the substituted atom are replaced. The substituent can be separated from the substituted atom by an alkyl chain or ethylene glycol chain, and can be terminated by an alkyl group.

Specific values described for radicals, substituents, and ranges, as well as specific embodiments of the invention described herein, are for illustration only; they do not exclude other defined values or other values within defined ranges, as would be recognized by one skilled in the art.

As used herein, the term "alkyl" refers to a branched, unbranched, or cyclic hydrocarbon having, for example, from 1 to about 30 carbon atoms, and often 1 to about 20, or 1 to about 12 carbon atoms. Examples include, but are not limited to, methyl, ethyl, 1-propyl, 2-propyl, 1-butyl, 2-methyl-1-propyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl 4-methyl-2-pentyl, 3-methyl-3-pentyl, 2-methyl-3-pentyl, 2,3-dimethyl-2-butyl, and 3,3-dimethyl-2-butyl, hexyl, octyl, decyl, or dodecyl. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

Alkoxy can be $(C_1-C_{12})$alkoxy, such as, for example, methoxy, ethoxy, propoxy, isopropoxy, butoxy, iso-butoxy, sec-butoxy, pentoxy, 3-pentoxy, hexyloxy, or octyloxy. Any alkyl or alkoxy (including an "alkoxy"-carbonyl) can be optionally unsubstituted or substituted.

The term "aryl" refers to a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like. Aryl can also refer to an unsaturated aromatic carbocyclic group of from 6 to 12 carbon atoms having a single ring (e.g., phenyl) or multiple condensed (fused) rings, wherein at least one ring is aromatic (e.g., naphthyl, dihydrophenanthrenyl, fluorenyl, or anthryl). The aryl can be unsubstituted or substituted.

As used herein, the term "mer" or "mers" refers to a unit of a polymer derived from a particular monomer. For example, a styrene mer refers to a segment of a polymer that was prepared from styrene to form polystyrene, e.g., a phenethyl group wherein the ethyl group is a 1,2-diradical. Accordingly, a mer can refer to a specific unit derived from an unsaturated monomer, thus indicating, for example, a phenethyl diradical within the polymerized chain.

The term "ethoxylated" refers to a group that includes one or more ethoxy (—O—CH₂—CH₂—) groups, for example, about 2 to about 24 ethoxy groups, or about 3 to about 12 ethoxy groups. An ethoxylated group that has two or more ethoxy or ethylene glycol groups refers to a polyethylene glycol, or PEG group. Ethoxylated or PEG groups can be terminated in an optionally substituted alkyl, for example, a methyl, or they can terminate with hydrogen, e.g., a 2-hydroxyethoxy group.

The terms "semifluorinated" and "at least partially fluorinated" refer to a group, for example an alkyl group, that has at least one hydrogen atom replaced by a fluorine atom. Semifluorinated groups include any carbon chains, or carbon chains that are interrupted by one or more heteroatoms (for example, oxygen), that contain one or more fluorine atoms. Typically the semifluorinated group will have one or more —CF₂— groups and can optionally terminate in a —CF₃ group. For example, the semifluorinated group can be a group of the formula:

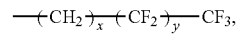

wherein each x is independently about 2 to about 20, and each y is independently 0 to about 20. In other embodiments, x can be about 3 to about 15, and y can be about 5 to about 15. Zonyl surfactants can be considered semifluorinated groups because a portion of the Zonyl surfactant group is a semifluorinated alkyl chain.

Zonyl® surfactants refer to ethoxylated fluoroalkyl chains with terminal alcohol groups. Zonyl® surfactants can be obtained from Dupont (Wilmington, Del.). These surfactants can be attached to appropriately functionalized block copolymers via the hydroxyl group, or via a halo group which has replaced the hydroxyl group. Accordingly, polymers having ethoxylated fluoroalkyl side chains can be prepared using any appropriate Zonyl® surfactant. One example of a suitable Zonyl® surfactant that can be used to prepare ethoxylated fluoroalkyl side chain-containing block copolymers is Zonyl FSO-100 [CAS #122525-99-9]. Other suitable Zonyl® surfactants include Zonyl FSN, Zonyl FSN-100, and Zonyl FSO.

Ethoxylated fluoroalkyl groups that can be used in various embodiments of the invention include moieties of formula Z:

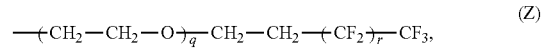

wherein each q is independently 0 to about 25; each r is independently 0 to about 18; and the moiety of formula Z is attached to a polymer chain or chain substituent through an ester, amide, ketone, carbamate, or amine, or an alkyl linking group.

The term "contacting" refers to the act of touching, making contact, or of bringing within immediate proximity.

The term "coating" refers to a manufacturing process or preparation for applying an adherent layer to a workpiece or substrate web. A coating can also be a layer of material that at least partially covers an underlying surface, such as a boat hull, pontoon, or any other surface in need of an antifouling coating.

The term "sporeling" refers to young plants derived from quadriflagellate, motile, pear-shaped, and asexual zoospores of *Ulva* that can settle on a surface by a process of selection, and germinate after attachment.

The term "halo" or "halide" refers to fluoro, chloro, bromo, or iodo.

Methods of Making Compounds, Polymers, and Coatings

Processes for preparing the compounds and surface-active polymers of the invention are provided as further embodiments of the invention. Related compounds and compositions can be prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., *Advanced Organic Chemistry*, $3^{rd}$ Ed., (John Wiley & Sons, New York, 1985), *Comprehensive Organic Synthesis. Selectivity, Strategy & Efficiency in Modern Organic Chemistry*, in 9 Volumes, Barry M. Trost, Ed.-in-Chief (Pergamon Press, New York, 1993 printing).

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be about $-100°$ C. to about $200°$ C., solvents will be aprotic or protic depending on the conditions required, and reaction times will be about 1 minute to about 10 days. Work-up of standard organic transformation reactions typically consists of quenching any unreacted reagents followed by partition between a water/organic layer system (extraction) and separation of the layer containing the product. Work-up of reactions with polymers typically consists of concentrating the reaction mixture by removing a quantity of solvent, followed by precipitation of the polymer using a solvent or solvent system in which the polymer has low or substantially no solubility, such as, for example, methanol, or a combination of water and methanol.

The polymers of the invention can be synthetically modified, resulting in various substitutions on the mers of the backbone polymer. The mers can be substituted with side groups, such as, for example, semifluorinated (SF), poly(ethylene glycol) (PEG), or ethoxylated fluoroalkyl side groups, or a combination thereof.

General and specific methods for preparing polymers, compositions, and coatings are described in U.S. Patent Application Publication No. US-2006-0083854, which is incorporated herein by reference. The polymers of the invention can be used as protective coatings for surfaces in need of antifouling properties. The coatings can form single layer coatings, bi-layer coatings, or multi-layer coatings. The preparation of bi-layer coatings has been described by Ober et al., U.S. Pat. No. 6,750,296, which is incorporated herein by reference. These techniques can be used to prepare bi-layer coatings that include the polymers described herein.

The invention also provides for a coating composition that includes a polymer as described herein, in combination with other ingredients. Such other ingredients can include, for example, a polymer, water, one or more solvents, additives, stabilizers, colorants, dispersants, or combinations thereof.

The invention also provides a method of at least partially coating a surface by contacting the surface with a composition containing a polymer as described herein. The coating procedure can be performed by brushing, immersing, pouring, solvent-casting, spin-coating, or spray-coating to contact the surface with the composition. Accordingly, the invention provides a method of coating or protecting a substrate, for example, a boat hull, from biofouling.

The surface coated by the composition can be a layer of a thermoplastic polymer. The thermoplastic polymer can at least partially covers a boat hull, pontoon, or any other structure in need of such a coating. The average-weight molecular weight of a polystyrene block of the a polymer that contains a quaternized nitrogen as described herein in the composition used to coat the thermoplastic polymer can be within about 20%, or about 10%, or about 5% of the average-weight molecular weight of the polystyrene block or blocks of a polymer comprising the thermoplastic polymer.

A bilayer can be formed and the bilayer can be annealed at a temperature above the glass transition temperature of the polystyrene blocks of the polymers in the bilayer. The coating can result in a top layer of about 30 nm to about 500 µm in thickness.

Specifically, the coating can result in a top layer of about 40 nm to about 150 µm in thickness. More specifically, the coating can result in a top layer of about 50 nm to about 25 µm in thickness.

The polymers can provide a sufficiently hydrophilic surface to prevent adsorption of extracellular matrices of settling organisms. These extracellular matrices can include proteins, glycoproteins, peptidoglycans, and nucleic acids that the organisms secrete for adhesion.

The amphiphilic nature of the ethoxylated fluoroalkyl chains of the polymers minimizes the adhesion strength of marine organisms. Many embodiments are readily soluble common solvents such as THF, toluene, $\alpha,\alpha,\alpha$-trifluorotoluene, methylene chloride, and chloroform. The polymers have good film forming properties. The polymers can have minimal or no solubility or swelling in water for under-water applications, and minimal or no toxicity.

Figure 10:
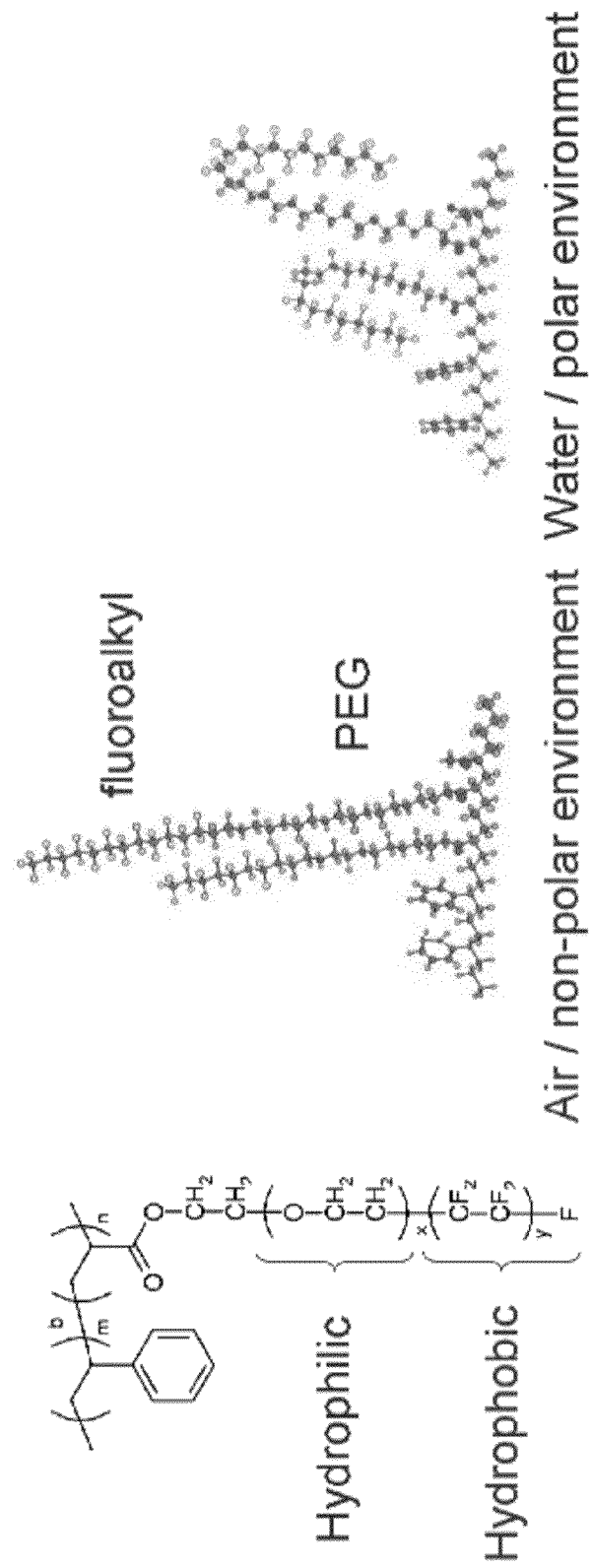
FIG. 10 illustrates the chemical structure of a comb-like block copolymer with amphiphilic side-chains according to an embodiment of the invention; wherein the fluoroalkyl portion of the side chain is hydrophobic and the ethoxylated ("PEGylated") portion of the side chain is hydrophilic. Also shown is a proposed mechanism for surface-reconstruction of the ethoxylated fluoroalkyl side-chains upon immersion of surface in water. The schematic in the middle indicates orientation of side chains in air while that on right shows the effect of water immersion.

The invention provides novel polymers with amphiphilic side chains and methods to prepare them. One embodiment is schematically shown in FIG. 10. PEG and fluoroalkyl units can be used for the amphiphilic side chains. In initial experiments, diatoms showed a higher release from surfaces of polymers with PEG side chains compared to that with semi-fluorinated side chains, whereas *Ulva* sporelings showed the opposite behavior (see Krishnan et al. *Biomacromolecules* 2006, 7, 1449-1462; and Youngblood et al. *Biofouling* 2003, 19, 91-98). Amphiphilic surface prepared from the polymers described herein result in low adhesion strength of both *Ulva* and *Navicula*.

In one embodiment it is possible to independently control the modulus and surface chemistry of the coatings by using a bilayer coating strategy. It is thus possible to have a sufficiently thick polymer film without using excessive amounts of the surface-active block copolymer (SABC). See Hexemer et al. *J. Polym. Sci.: Part B: Polym. Phys.* 2004, 42, 411-420. The bottom layer of this coating can be a polystyrene-block-poly(ethylene-ran-butylene)-block-polystyrene (SEBS, KRATON G1652) and the top-layer can be a polymer as described herein, for example, the block copolymer shown in FIG. 10. The role of the polystyrene block in the SABC is to increase the compatibility of the SEBS and SABC layers by entrapment in the cylindrical polystyrene domains at the SEBS surface.

Accordingly, the invention provides polymers, methods of preparing polymers, and compositions that include polymers, wherein said polymers include a plurality of two-carbon repeating units in a polymer chain, wherein one or more of the two-carbon repeating units of the polymer chain have a substituent that is covalently bonded to a moiety of formula Z:

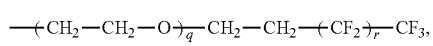
(Z)

wherein q is independently 1 to about 25; r is independently 0 to about 18; and the moiety of formula Z is attached to the polymer chain substituent through an ester, amide, ketone, carbamate, or amine.

The polymer can include other types of chain substituents, for example, one or more polymer chain substituents selected from aryl groups, alkyl groups, and alkoxycarbonyl groups, wherein any alkyl, aryl, or alkoxy is optionally substituted with one or more alkyl, alkoxy, hydroxy, halo, dialkylamino, trifluoromethyl, ethylene glycol, or perfluoroalkyl groups. The two-carbon repeating units in the polymer chain can include polystyrene units, polyisoprene units, polybutadiene units, polyacrylate units, polymethacrylate units, or a combination thereof, among other types of polymer units.

The polymer chain substituent can be, for example, a carboxy group and the moiety of formula Z can be attached to the carboxy group to form an ester linkage.

The invention also provides a polymer that includes formula I:

a moiety of formula Z:

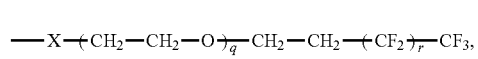
(Z)

wherein each X is independently —O—C(=O)—CH$^2$—O—, —NH—C(=O)—CH$_2$—O—, or —NH—, linking the moiety of formula Z to the carbon attached to R$^3$, each q is independently 1 to about 25, and each r is independently 1 to about 18;

provided that at least one R$^3$ of formula I is a moiety of formula Z;

each R$^4$ and R$^5$ is independently hydrogen, R$^3$, or absent, provided that when R$^4$ is hydrogen, R$^5$ is R$^3$; and when R$^4$ is R$^3$, R$^5$ is hydrogen; and each individual bond represented by—is an optional double bond, provided that when the bond between the carbons of R$^4$ and R$^5$ is present, R$^4$ and R$^5$ are absent.

In one embodiment, each X can be —O—C(=O)—CH$_2$—O—, q can be 1 to about 15, and r can be 0 to about 8.

The invention further provides a polymer that includes formula (II):

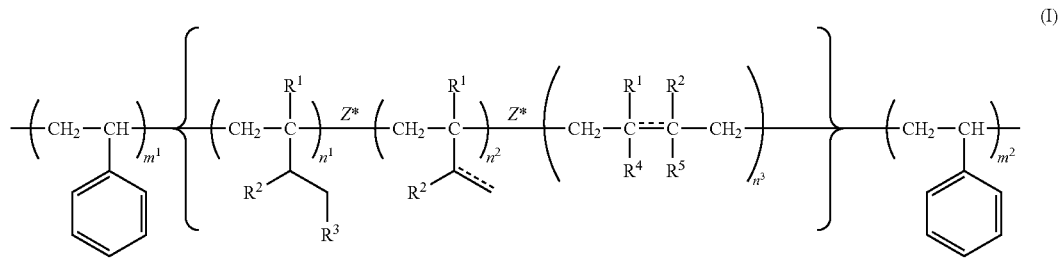
(I)

wherein m$^1$ is about 5 to about 2000;
m$^2$ is absent or is independently about 5 to about 2000;
n$^1$ is about 5 to about 2,000;
n$^2$ is absent or is independently about 5 to about 2000;
n$^3$ is absent or is independently about 5 to about 2000;
the dispersement of each individual n$^1$, n$^2$, and n$^3$ subunit on either side of either z* is random and each individual n$^1$, n$^2$, and n$^3$ subunit occurs interchangeably with any other n$^1$, n$^2$, or n$^3$ subunit within the brackets of formula I;

each R$^1$ is independently hydrogen or methyl and each R$^2$ is independently hydrogen or methyl provided that at least one of R$^1$ and R$^2$ within each n subunit is hydrogen;

each R$^3$ is independently H, OH, or halo; or alkyl wherein alkyl is optionally at least partially fluorinated; alkyl-terminated (-ethylene glycol-)$_n$ wherein n is about 2 to about 24; wherein each alkyl or alkyl-terminated (-ethylene glycol-)$_n$ is covalently bonded to the carbon of R$^3$ through an ester, amide, or amino group; or

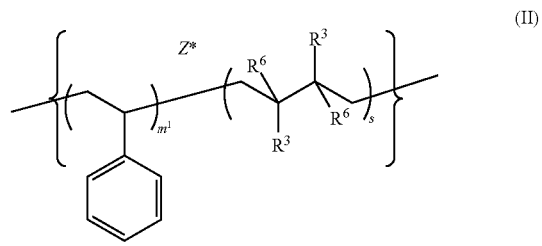
(II)

wherein m$^1$ is about 5 to about 2000;
s is about 5 to about 2000;
each R$^6$ is independently H or alkyl, provided that when one R$^6$ of any given subunit s is alkyl, the other R$^6$ of the same subunit s is H;
each R$^3$ is independently H, OH, halo, carboxy, or
alkyl wherein alkyl is optionally at least partially fluorinated; alkyl-terminated (-ethylene glycol-)$_n$ wherein n is about 2 to about 24; wherein each alkyl or alkyl-terminated (-ethylene glycol-)$_n$ is covalently bonded to the carbon of R$^3$ through an ester, amide, or amino group; or a moiety of formula Z:

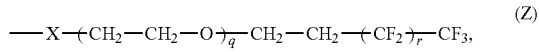

wherein each X is independently —C(=O)—O— or —C(=O)—NH—, linking the moiety of formula Z to the carbon attached to $R^3$, each q is independently 1 to about 25, and each r is independently 1 to about 18;

provided that when one $R^3$ of any given subunit s is a moiety of formula Z, the other $R^3$ of the same subunit s is not a moiety of formula Z;

provided that at least one $R^3$ of formula II is a moiety of formula Z; and the dispersement of each individual s subunit and each individual $m^1$ subunit on either side of z* is random and each individual s subunit and each individual $m^1$ subunit occurs interchangeably with any other s or $m^1$ subunit within the brackets of formula II.

In one embodiment, each X can be —C(=O)—O—, q can be 1 to about 15, and r can be 0 to about 8.

The polymer can be a random polymer, or alternatively, a block copolymer, depending on the process used to prepare the polymer. The polymer can have a molecular weight of about 5 kDa to about 2,000 kDa. Other embodiments can have a molecular weight of about 3 kDa to about 500 kDa, about 5 kDa to about 1,000 kDa, about 50 kDa to about 1,500 kDa, or about 100 kDa to about 2,000 kDa.

The moiety of formula Z can include values of q and r wherein each q is 1 to about 15 and each r is 0 to about 8.

The polymer can exhibit antifouling properties toward one or more of marine algae, algal spores, bacterial cells, diatoms, and protozoa.

The invention also provides an antifouling surface that includes a surface coating that includes a polymer as described above. The antifouling surface can optionally include a base layer. The base layer can be, for example, an elastomeric polymer. The invention also provides a coating composition that includes a polymer as described herein in combination with one or more of a polymer, water, and one or more solvents.

The invention further provides a method that includes at least partially coating a surface by contacting the surface with a coating composition that includes a polymer as described herein. The contacting can be performed by brushing, immersing, pouring, solvent-casting, spin-coating, or spray-coating the surface with the composition.

The surface can include a layer of a thermoplastic polymer. The thermoplastic polymer can at least partially cover a boat hull. The average weight molecular weight of a polystyrene block of a polymer as described herein in solution used to coat the thermoplastic polymer can be within about 10% of the average weight molecular weight of the polystyrene block or blocks of a polymer comprising the thermoplastic polymer. A bilayer can be formed and the bilayer can be annealed at a temperature above the glass transition temperature of a polystyrene block of the bilayer. The coating can result in a layer of about 50 nm to about 150 μm in thickness.

In any polymer of the invention, the terminal groups of the polymer will be determined by the method of polymerization used and the respective initiator and quench used in the preparation process. One skilled in the art will readily understand the variety of terminal groups that can be provided by the initiators and quenching agents. Typical end groups include sec-butyl, bromo, and various N-alkoxyamine and dithioester groups. Other terminal groups derived from the quenching agent include hydrogen, and various silyl derivatives, for example, a dimethyl(2-perfluorooctyl)ethylsilyl group.

The variables and limitations described for one general or specific embodiment for any polymer described herein can also be applied to other embodiments, for example, other variations of the polymer of the invention and variations of the embodiments provided in the Examples.

In certain embodiments, the polymers of the invention allow environment dependent surface reconstruction by simple flipping of the side-chains, as depicted in FIG. 10. Other architectures would require mesoscale rearrangement of the hydrophobic and hydrophilic domains to effect a similar polarity change. It is expected that when a surface is covered by a thin layer of the ethoxylated fluoroalkyl side chains, as shown in FIG. 10, any change in surface polarity would occur uniformly throughout the surface, without complex topographic changes.

The following Examples are intended to illustrate the above invention and should not be construed as to narrow its scope. One skilled in the art will readily recognize that the Examples suggest many other ways in which the present invention could be practiced. It should be understood that many variations and modifications may be made while remaining within the scope of the invention.

EXAMPLES

Materials: Styrene (CAS #100-42-5, FW 104.15, Aldrich, 99%) was passed through a column of basic alumina to remove the 4-tert-butylcatechol inhibitor. Tert-butyl acrylate (tBA, CAS #1663-39-4, FW 128.17, Aldrich, 98%) containing 10-20 ppm of monomethyl ether hydroquinone as inhibitor was extracted with 5% aqueous NaOH and then washed with distilled water. After drying over calcium chloride, the monomer was distilled under vacuum.

Copper (I) bromide (CAS #7787-70-4, CuBr, FW 143.45, Aldrich, 99.999%), copper(II) bromide (CAS #7789-45-9, $CuBr_2$, FW 223.35, Aldrich, 99.999%), 1,1,4,7,7-pentamethyldiethylenetriamine (PMDETA, CAS #3030-47-5, $[(CH_3)_2NCH_2CH_2]_2NCH_3$, FW 173.30, Aldrich, 99%), methyl 2-bromopropionate (MBP, CAS #5445-17-0, $CH_3CH(Br)CO_2CH_3$, FW 167.00, Aldrich, 98%), 1,3-dicyclohexylcarbodiimide (DCC, CAS #538-75-0, $C_6H_{11}N{=}C{=}NC_6H_{11}$, FW 206.33, Aldrich, 99%), 4-dimethylaminopyridine (DMAP, CAS #1122-58-3, $(CH_3)_2NC_5H_4N$, FW 122.17, Aldrich, 99%), anhydrous pyridine (99.8%), acetone (99.5%) and anhydrous tetrahydrofuran (THF) were obtained from Sigma-Aldrich and used without further purification.

The ethoxylated fluoroalkyl surfactant, Zonyl® FSO-100 (registered trademark of E. I. du Pont de Nemours & Co., Inc.; CAS #122525-99-9), was also obtained from Sigma-Aldrich. The average molecular weight of Zonyl® FSO-100, $F(CF_2CF_2)_3CH_2CH_2O(CH_2CH_2O)_xH$ (x=0 to 15 and y=1 to 7), reported by the supplier is about 725 g/mol.

3-(Glycidoxypropyl)trimethoxysilane (GPS, CAS #2530-83-8) was purchased from Gelest. Polystyrene-block-poly (ethylene-co-butylene)-block-polystyrene (SEBS) triblock thermoplastic elastomer (KRATON G1652M), and SEBS grafted with maleic anhydride (MA-SEBS, KRATON FG1901X) were received from KRATON polymers.

Methanol, toluene (technical grades, Fisher), 96% sulfuric acid, 30 wt % hydrogen peroxide in water, 95% ethanol, and all other reagents were used as received.

Example 1

Polymer Synthesis and Characterization

Polymer analogous reactions have previously been used to prepare polymers with functional side chains. Wang et al. (*Macromolecules* 1997, 30, 1906-1914) have prepared block copolymers with semifluorinated side chains by introducing hydroxyl groups in the polyisoprene block of polystyrene-block-polyisoprene followed by esterification with semifluorinated carboxylic acids. Hourdet et al. (*Polymer* 1997, 38, 2535-2547) synthesized poly(acrylic acid)-graft-poly(ethylene glycol) by reacting ω-amino PEG with poly(acrylic acid). Poly(methacrylic acid)-graft-poly(ethylene glycol) has been similarly prepared by Poe et al. (*Macromolecules* 2004, 37, 2603-2612).

The synthesis of polystyrene-block-poly(tert-butyl acrylate) used in this work was based in part on a procedure reported by of Davis and Matyjaszewski (*Macromolecules* 2001, 34, 2101-2107). The tert-butyl acrylate (tBA) block was quantitatively hydrolyzed to acrylic acid using concentrated HCl. Esterification at room temperature using DCC and DMAP resulted in a high degree of attachment of the fluorinated PEG (Zonyl FSO-100) to the acrylic acid backbone, as illustrated below in Scheme 1. The extent of attachment, calculated from the ratios of —COOCH$_2$CH$_2$— protons of the side chains and the aromatic protons of styrene, was close to 95%.

green, 1.6 mmol of MBP was added using a syringe, and the monomer was polymerized for 6 hours at 60° C. After cooling the reaction mixture to room temperature, 50 mL of acetone was added and the polymer solution treated with neutral alumina to remove the copper salts. Acetone was removed by evaporation, and the polymer further purified by dissolving in diethyl ether and precipitating in methanol/water mixture (1:1 v/v) at 0° C. Drying under vacuum resulted in a polymer with a molecular weight of about 3000 g/mol and a polydispersity index of 1.1.

$^1$H NMR (300 MHz, CDCl$_3$, δ): 1.5 (s, 9H, —C(CH$_3$)$_3$); 1.85 and 2.35 (br s, —CH$_2$, >CH—); 3.75 (s, 3H, —OCH$_3$ from initiator); 4.1 (m, 1H, >CH—Br). IR (dry film) $\tilde{v}_{max}$ (cm$^{-1}$): 2977 (C—H stretching, tert-butyl); 2929 (C—H stretching, backbone); 1727 (C=O stretching, ester); 1367 (C—H bending, tert-butyl).

Poly(tert-butyl acrylate)-block-polystyrene (II). Two grams (0.67 mmol) of the bromo-terminated poly(tBA) and 0.95 mmol of CuBr were taken in a round-bottom flask. Deoxygenated styrene (95 mmol) was added to the reactor and stirred until it dissolved the polymer. PMDETA (0.95 mmol) was injected to form a complex with CuBr. Polymerization at 100° C. for 120 minutes resulted in a viscous liquid that was dissolved in 150 mL of tetrahydrofuran after cooling to room temperature. The solution was passed through a column of neutral alumina to remove copper salts, concentrated by evaporation of the solvent, and precipitated in excess of methanol. After re-precipitation in methanol, the

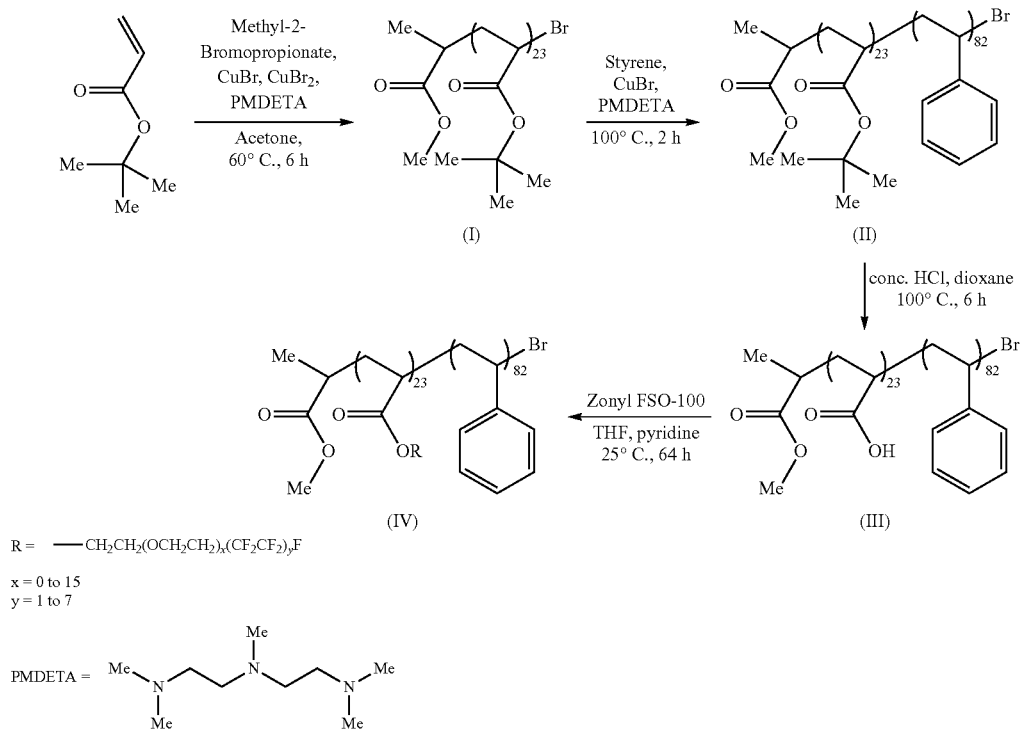

Scheme 1. Synthesis of Block Copolymers with Ethoxylated Fluoroalkyl Side-chains Poly(tert-butyl acrylate) macroinitiator (I). A mixture of acetone (3 mL), 80 mmol of tBA and 0.8 mmol PMDETA, deoxygenated by purging nitrogen, were added to 0.8 mmol of CuBr and 0.04 mmol of CuBr$_2$ taken in a round-bottom flask. After complex formation, evident from the change in the appearance of solution from colorless to clear and light polymer was dried under vacuum at room temperature. Gel permeation chromatography indicated a polydispersity index of 1.1.

$^1$H NMR (300 MHz, CDCl$_3$, δ): 1.5 (s, 9H, —C(CH$_3$)$_3$); 1.85 and 2.35 (br s, —CH$_2$, >CH—); 6.5 AND 7.1 (br s, 5H, styrene). IR (dry film) $\tilde{v}_{max}$ (cm$^{-1}$): 3026 (C—H stretching, aromatic); 2976 (C—H stretching, tert-butyl); 2926 (C—H stretching, backbone); 1728 (C=O stretching, ester); 1493, 1452 (C=C stretching, aromatic); 1367 (C—H bending, tert-butyl); 758 and 700 (C—H bending, aromatic).

Poly(acrylic acid)-block-polystyrene (III). Two milliliters of concentrated hydrochloric acid solution (12 N) was added to a 10% w/v solution of poly(tert-butyl acrylate)-block-polystyrene in dioxane, and the solution refluxed for about 6 hours. The polymer was recovered by cooling the dioxane solution and precipitation from water. Complete hydrolysis of tert-butyl acrylate was confirmed by the disappearance of IR absorbances at 2976 cm$^{-1}$ and 1367 cm$^{-1}$, corresponding to C—H stretching and bending, respectively, of the tert-butyl groups.

$^1$H NMR (300 MHz, DMSO-d$_6$, δ): 2.2 and 1.6 (br s, —CH$_2$, >CH—); 6.5 and 7.1 (br s, 5H, styrene); 12.0 (br s, COOH). IR (dry film) $\bar{v}_{max}$ (cm$^{-1}$): 3600-2400 (O—H stretching, carboxylic acid); 3026 (C—H stretching, aromatic); 2926 (C—H stretching, backbone); 1716 (C=O stretching, ester); 1492, 1452 (C=C stretching, aromatic); 758 and 700 (C—H bending, aromatic).

Poly(ethoxylated fluoroalkyl acrylate)-block-polystyrene (IV). One gram of poly(acrylic acid)-block-polystyrene (2.19 mmol acrylic acid) was dissolved in 5 mL of anhydrous pyridine. DCC (6.57 mmol), DMAP (0.823 mmol), and Zonyl FSO-100 (6 g) were dissolved in tetrahydrofuran and added drop-wise to the polymer solution. The reaction mixture was stirred at room temperature for about 2.5 days. Dicyclohexylurea formed during the reaction was removed by filtration. After concentration under reduced pressure, the polymer solution was poured into excess methanol. Further purification was achieved by precipitating the polymer from tetrahydrofuran into methanol.

$^1$H NMR (300 MHz, CDCl$_3$, δ): 6.5 and 7.1 (5H, styrene); 4.16 (br s, 2H, —COOCH$_2$—); 3.77 (t, 2H, —COOCH$_2$CH$_2$—); 3.64 (br s, —OCH$_2$CH$_2$O—); 2.42 (m, 2H, —CH$_2$CF$_2$—); 1.86, 1.43 (backbone); $^{19}$F NMR (282.24 MHz, CDCl$_3$, CF$_3$COOH reference, δ): −126.65, −124.16, −123.38, −122.41, −113.95, −81.27 (3F, —CF$_3$). IR (dry film) $\bar{v}_{max}$ (cm$^{-1}$): 3026 (C—H stretching, aromatic); 2922 (C—H stretching, backbone); 1731 (C=O stretching, ester); 1490, 1450 (C=C stretching, aromatic); 1400-1000 (C—F stretching); 754 and 698 (C—H bending, aromatic).

Gel permeation chromatography of THF solution of polymers (1 mg/mL) was carried out using four Waters Styragel HT columns operating at 40° C., and Waters 490 ultraviolet (254 nm wavelength) and Waters 410 refractive index detectors. The molecular weight range of the columns was from 500 to 10$^7$ g/mol. THF was used as the eluent at a flow-rate of 1 mL/min, and toluene used as marker for flow calibration. The IR spectra of the polymers cast as a films from THF solution on sodium chloride or potassium bromide salt plates were collected using a Mattson 2020 Galaxy Series FTIR spectrometer. $^1$H and $^{19}$F NMR spectra were recorded using Varian Gemini spectrometer with deuterated solvents. Matrix-assisted laser desorption ionization-time of flight (MALDI-TOF) mass spectroscopy of the ethoxylated fluoroalkyl surfactant was performed using an Applied Biosystems 4700 Proteomics Analyzer with 4-hydroxy-3,5-dimethoxy-cinnamic acid (CAS #530-59-6) as matrix.

Molecular weight, its distribution, and block copolymer composition. The GPC molecular weight distributions of poly(tBA), poly(tBA)-block-PS and the block copolymer with ethoxylated fluoroalkyl side chains showed that all the polymers had a relatively narrow polydispersity index. The degree of polymerization of the tBA block, determined by $^1$H NMR using the backbone>CH— and terminal>CH—Br peaks, was found to be 23. Using the protons attached to the aromatic ring of styrene, and all the protons in the block copolymer, the molar percent of styrene units in the polymer was determined to be 78%. Thus, the degree of polymerization of the polystyrene block is about 82. The molecular weight of the PS block (about 8500 g/mol) is close to that of the PS blocks in SEBS.

The fluorinated PEG, F(CF$_2$CF$_2$)$_y$(CH$_2$CH$_2$O)$_x$CH$_2$CH$_2$OH, used for attachment has a broad distribution of molecular weights, with x=0 to 15 and y=1 to 7 specified by the supplier. MALDI-TOF spectroscopy showed two species with mass-to-charge ratios of 695.25 g/mol (y=5, x=3) and 739.28 g/mol (y=5, x=4) as the major components. Molecules with y=5, x=5, 6, and y=2, x=6 to 12 could also be identified as other components in the mixture. Based on the areas of CF$_2$CH$_2$ protons and CF$_3$ fluorines in $^1$H and $^{19}$F NMR spectra, respectively, the average composition was determined to be y=3.4±0.7 and x=5.9±1.0. After reaction with polystyrene-block-poly(acrylic acid), the average composition of the side chain, determined by NMR spectroscopy, was y=3.0±0.7 and x=3.5±0.6.

Example 2

Surface Characterization and Analysis

In this Example, contact angle measurements, near-edge X-ray absorption fine structure spectroscopy (NEXAFS), X-ray photoelectron spectroscopy (XPS), and scanning force microscopy (SFM) experiments are described to illustrate the chemical composition and morphology of the surfaces and the fouling-release properties of the coatings, according to various embodiments of the invention, using *Ulva* zoospores and sporelings and the diatom *Navicula*.

Samples for surface characterization were prepared by spin-coating a 3% (w/v) solution of the amphiphilic block copolymer prepared in Example 1 on silicon wafers using a Cee® Model 100CB spin-coater at 2000 rpm (acceleration of 1000 rpm/s) for 30 seconds. The surfaces were dried in a low-vacuum oven at 60° C. for 12 hours before further annealing at 120° C. or 150° C. in a high-vacuum oven. Test surfaces for biofouling assays were prepared on 3 inch×1 inch glass microscope slides. The glass slides were cleaned in hot piranha solution (conc. sulfuric acid+30 wt % hydrogen peroxide solution, 7:3 v/v), rinsed with distilled water and dried using nitrogen.

A 2% (w/v) solution of (3-glycidoxypropyl)trimethoxysilane in 95% ethanol (with pH adjusted between 4.5 and 5 using acetic acid) was prepared by adding the silane to the ethanol solution and stirring for 5 minutes. The glass slides were then soaked in this solution for at least 1 hour, rinsed with ethanol and heated in an oven at 110° C. for 10 minutes. The GPS functionalized glass slides were spin-coated with a toluene solution containing 5% (w/v) of MA-SEBS, and 2% (w/v) SEBS, and annealed in a vacuum-oven at 120° C. for 12 hours. The styrene content of both SEBS and MA-SEBS was 30 wt %, and the latter had 1.4-2.0 wt % of grafted maleic anhydride. The maleic anhydride groups in the polymer backbone react with epoxy groups on the glass surface, improving the bonding of the coating to the glass.

The surfaces were further spin-coated three times with 12% (w/v) solution of SEBS in toluene (2500 rpm) followed by vacuum-annealing at 120° C. for 12 hours. A 1.5% (w/v) solution of the amphiphilic block copolymer was spray-coated on the SEBS surface using Badger Model 250 airbrush and 50 psi nitrogen gas to obtain a polymer surface-density of 1.5 to 2 mg/cm². The surfaces were finally dried in a low-vacuum oven at 60° C. for 18 hours (or 60° C. for 18 hours and 120° C. for 6 hours) to ensure complete removal of solvents and to study the effect of annealing on antifouling properties. The fouling-release properties of surfaces prepared under two different annealing conditions were compared.

Contact angles were measured using a NRL contact angle goniometer (Ramé-Hart Model 100-00) at room temperature. Dynamic water contact angle measurements were performed by addition and retraction of a drop of water on the surface. The contact angle of an air-bubble over the polymer surface immersed in water was determined using the captive bubble method (Adamson, A. W. Physical Chemistry of Surfaces, $3^{rd}$ ed., Wiley: New York, 1976; Andrade et al. *J. Polym. Sci. Polym. Symp.* 1979, 66, 313-336). An air-bubble snapped off from the tip of a 22 gauge stainless steel syringe (0.7 mm O.D. and 0.4 mm I. D.) was contacted with the surface immersed in water, and the contact angle measured. The angles reported are those between the surfaces and the air bubble, measured on the water-side. Thus, a low captive-bubble contact angle indicates a hydrophilic surface, while a higher angle indicates a more hydrophobic surface.

Surface roughness was determined using a 3-D interferometric non-contact surface profiler (ADE Phase-Shift MicroAXM-100HR). Root-mean-square (rms) roughness values were determined over regions of 631 μm×849 μm size and averaged over at least 10 measurements. The surface morphology and surface roughness on a local scale were studied using a Veeco Dimension 3100 Scanning Probe Microscope in the tapping mode.

The X-ray photoelectron spectroscopy (XPS) measurements were performed using an Axis Ultra XPS system (Kratos) with a monochromatic Al Kα X-ray source (1486.6 eV) operating at 225 W under $7.0 \times 10^{-9}$ torr vacuum. Charge compensation was carried out by injection of low energy electrons into the magnetic lens of the electron spectrometer. The pass energy of the analyzer was set at 40 eV. The energy resolution was set at 0.1 eV with a dwell time of 500 ms. The spectra were analyzed using CasaXPS v. 2.1.9 software.

NEXAFS experiments were carried out on the U7A NIST/Dow materials characterization end-station at the National Synchrotron Light Source at Brookhaven National Laboratory. The principles of NEXAFS and description of the BNL beamline have been outlined by Ober and coworkers (Genzer et al. in: *Applications of Synchrotron Radiation Techniques to Materials Science IV*, Mini, S. M.; Perry, D. L.; Stock, S. R.; Terminello, L. J. (Eds.), MRS Symposium Proceedings, Vol. 524, p. 365; and Genzer at al. *Langmuir*, 2000, 16, 1993-1997). The NIST/Dow materials characterization end-station was equipped with a sample holder positioned on a goniometer, which controlled the orientation of the sample with respect to the polarization vector of the X-rays. The partial-electron-yield (PEY) signal was collected using a channeltron electron multiplier with an adjustable entrance grid bias (EGB). Unless specified, all the reported data are for a grid bias of −150 V. The channeltron PEY detector was positioned at an angle of 45° with respect to the incoming X-ray beam, and in the equatorial plane of the sample chamber.

To eliminate the effect of incident beam intensity fluctuations and monochromator absorption features, the PEY signals were normalized by the incident beam intensity obtained from the photo yield of a clean gold grid. A linear pre-edge baseline was subtracted from the normalized spectra, and the edge jump was arbitrarily set to unity at 320 eV, far above the edge, a procedure that enabled comparison of different NEXAFS spectra for the same number of carbon atoms within the Auger electron escape depth of the sample surface (Samant et al. *Macromolecules* 1996, 29, 8334-8342). The photon energy was calibrated by adjusting the peak position of the lowest π* phenyl resonace from polystyrene to 285.5 eV (Liu et al. *Macromolecules* 1997, 30, 7768-7771). Each measurement was taken on a fresh spot of the sample in order to minimize possible beam damage effects.

Biofouling Assays.

Leaching. Slides were incubated at about 20° C. for 3 days in a 30 L tank of recirculating deionized water. Equilibration with seawater was achieved by transferring the slides to dishes containing artificial seawater one hour prior to the start of the experiment.

Settlement of zoospores. Fertile plants of *Ulva linza* were collected from Wembury Beach, England (50°18' N; 4°02' W). Zoospores were released and prepared for attachment experiments as described by Callow et al. *J. Phycol.* 1997, 33, 938-947). Ten-milliliter of zoospore suspensions were pipetted into individual compartments of polystyrene culture dishes (Fisher) each containing a glass microscope slide. The dishes were incubated in the dark at about 20° C. After 1 hour the slides were gently washed in seawater to remove zoospores that had not attached. The density of zoospores attached to the surface was counted on each of 3 replicate slides using an image analysis system attached to a fluorescent microscope. Spores were visualized by autofluorescence of chlorophyll. Counts were made for 30 fields of view (each 0.17 mm²) on each slide.

Growth of sporelings. Spores were allowed to settle for 1 hour in darkness. After washing, sporelings were cultured in enriched seawater medium in individual (10 mL) wells in polystyrene dishes under illuminated conditions. The medium was refreshed every 2 days and the sporelings cultured for 8 days. Strength of attachment of sporelings was assessed using a wall shear stress of 53 Pa in a turbulent flow channel (see Schultz et al. *Biofouling* 2000, 15, 243-251).

Sporeling biomass was determined in situ by measuring the fluorescence of the chlorophyll contained within the sporelings using a Tecan fluorescent plate reader. The biomass is quantified in terms of relative fluorescent units (RFU). The RFU value for each slide is the mean of 196 point fluorescence readings. The data are expressed as the mean RFU of six replicate slides; error bars show standard error of the mean.

*Navicula* settlement and strength of attachment. *Navicula* cultures were prepared as described in Holland et al. (*Biofouling* 2004, 20, 323-329). Ten mL of the cell suspension were added to individual compartments of polystyrene culture dishes (Greiner Bio-1) each containing a glass microscope slide. After 2 hours in the light at about 20° C., the slides were very gently washed in seawater to remove cells which had not properly attached. The density of cells attached to the surface was counted on each slide using an image analysis system attached to a fluorescent microscope. Counts were made for 30 fields of view (each 0.17 mm²) on each slide.

Slides settled with *Navicula* were exposed to shear stress in a water channel. The number of cells remaining attached was compared with unexposed control slides (used to determine settlement as above). Cells were counted using the image analysis system as described above.

*Ulva* and *Navicula* assays were performed on the spray-coated amphiphilic surfaces vacuum-dried at 60° C. In addition, surfaces annealed at 120° C. were also tested with *Ulva* to study the effect of annealing on antifouling properties. Acid washed glass slides and glass slides coated with poly (dimethyl siloxane) were used as standards. The acid washed glass slides were prepared by washing in Decon detergent before soaking in 1 M hydrochloric acid for 24 hours. The PDMS surfaces were prepared using Silastic® T-2 mixture from Dow-Corning Corporation, as described in Hoipkemeier-Wilson et al. (*Biofouling* 2004, 20, 53-63). Ten parts by weight of Silastic® T-2 poly(dimethyl siloxane) mixed with 1 part by weight of Silastic® T-2 poly(methyl silane) crosslinking agent was applied to glass microscope slides and cured at 50° C. for 5 hours. The glass slides were functionalized with allyltrimethoxy silane to covalently attach the PDMS coating to the substrate.

Water contact angle measurements. A 3% (w/v) chloroform solution of the block copolymer with ethoxylated fluoroalkyl side chains (as prepared in Example 1) was spin-coated on a silicon wafer and vacuum dried at 60° C. for about 24 hours. The advancing and receding water contact angles were determined to be $(94\pm1)°$ and $(34\pm1)°$, respectively. The contact angle of an air-bubble on the surface immersed in water decreased from $(55\pm2)°$ immediately after immersion to $(46\pm2)°$ after a day, $(41\pm2)°$ after 3 days, and reached an equilibrium value of $(31\pm2)°$ after about 2 weeks.

The decrease in the contact angle is attributed to the migration of the PEG segments to the water-polymer interface. Such a molecular reorganization of the surface can occur by: (i) the migration of the polystyrene block away from the interface, and (ii) the reorientation of the side-chains by the proposed mechanism illustrated in FIG. 10. In the latter case, the flipping of the side-chains would enhance the enthalpically favorable interaction of PEG with water, while simultaneously minimizing water-contact of the hydrophobic fluoroalkyl segments.

The equilibrium surface structure, from the point of view of the minimization of enthalpy, would be one in which the polystyrene block and the fluoroalkyl segments are completely buried under the PEG groups. That the actual surface morphology is close to the expected picture is corroborated by the equilibrium value of the captive-bubble contact angle (~31°), which is similar to that for surface-tethered PEGylated polymer brushes in contact with water (see Andruzzi et al. *Langmuir* 2005, 21, 2495-2504).

The advancing and receding water contact angle measurements in air indicate that the molecular reorganization occurs over a short time-scale (corresponding to the rate of addition and retraction of the water drop). These measurements possibly reflect molecular reorganization by flipping of the side chains. On the contrary, the captive air-bubble contact angle measurements indicate surface reconstruction over a period of days. This slower reconstruction is attributed to the migration of the polystyrene block away from the surface and the fluorinated block toward the surface.

The under-water octane contact angle was $(55\pm5)°$. From the captive air-bubble and octane drop contact angles, the polymer-water interfacial energy could be estimated to be about 4 mJ/m² (see Andrade et al. *J. Polym. Sci. Polym. Symp.* 1979, 66, 313-336), a fairly low value as would be expected for a hydrated PEGylated surface. The advancing and receding water contact angles on the spray-coated amphiphilic surfaces with SEBS bottom layers were $(97\pm3)°$ and $(42\pm5)°$ with no significant difference between surfaces annealed at 60° C. and 120° C.

Near-Edge X-Ray Absorption Fine Structure Spectroscopy. FIG. 1 shows the NEXAFS spectrum of a surface prepared by spin-coating a 3% (w/v) solution of the amphiphilic block copolymer in chloroform. After drying in a vacuum oven at 60° C., the surface was further annealed at 120° C. for 12 hours. The NEXAFS spectrum was obtained at an X-ray incidence of 55° to the surface-normal. The entrance grid bias of the channeltron PEY detector was −150 V. The experimental spectrum was deconvoluted by performing a non-linear least-squares fit using a series of Gaussian peaks for resonances corresponding to bound state transitions and a Gaussian step multiplied by an exponential decay for the continuum step (see Stöhr, J. NEXAFS Spectroscopy, Springer-Verlag: New York, 1996; Chapter 7, p. 211).

Peak assignments were made based on calibrated NEXAFS spectra of polystyrene, poly(ethylene oxide), and poly (methyl methacrylate) reported in the literature (Liu et al. *Macromolecules* 1997, 30, 7768-7771; Wang et al. *Macromolecules* 1997, 30, 1906-1914; and Andruzzi et al. *Langmuir* 2005, 21, 2495-2504, respectively). The phenyl ring C $1s \rightarrow \pi^*_{C=C}$ resonance occurs at 285.5 eV. The resonance at 287.7 eV is due to the $1s \rightarrow \sigma^*_{C-H}$ transitions. The peak at 289 eV is attributed to $1s \rightarrow \pi^*_{C=C}$ resonance while that at 299 eV is probably a C=O σ* resonance. The $\sigma^*_{C-F}$, $\sigma^*_{C-O}$ and $\sigma^*_{C-C}$ transitions, corresponding to the amphiphilic side-chains, result in the peaks at 293 eV and 295.8 eV. The continuum step was found to be located near 290 eV. The intensity of the $1s \rightarrow \sigma^*_{C-F}$ peak at 293 eV shows a weak and non-monotonic relationship when plotted against $\sin^2 \theta$, where θ is the incidence angle of X-ray, indicating that the fluoroalkyl tail of the ethoxylated fluoroalkyl side-chains are unoriented with respect to the surface normal.

Unlike polymers with long semifluorinated alkyl side-chains, the ethoxylated fluoroalkyl side chains thus appear not to form a smectic liquid crystalline phase. The lack of liquid-crystallinity was also evident from the absence of melting peaks in differential scanning calorimetry (DSC) of the block copolymer. This may be due to the polydispersity of the ethoxylated fluoroalkyl side chains. Zonyl FSO-100 has a broad distribution of perfluoroethylene and ethoxy group lengths. The difference in the lengths of the poly(ethylene oxide) spacer is expected to hinder liquid crystalline packing of the fluoroalkyl tails.

Figure 2:
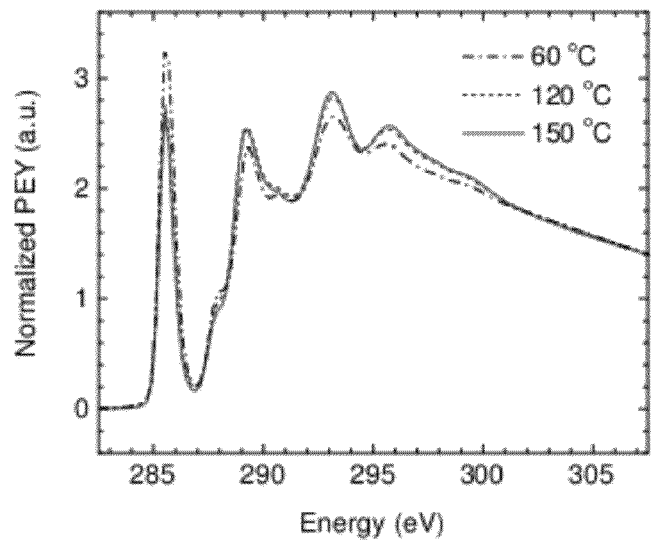
FIG. 2 illustrates a NEXAFS spectra at X-ray incident angle of 55° to the normal of surfaces prepared by spin-coating a 3% (w/v) solution of the block copolymer in chloroform and (a) vacuum-drying at 60° C. for 12 hours, followed by (b) annealing at 120° C. for 12 hours, and (c) annealing at 150° C. for 12 hours.

Effect of annealing temperature. FIG. 2 shows the NEXAFS spectra of surfaces annealed at three different temperatures. Two observations are noteworthy. First, the intensity of C=C π* peak corresponding to the polystyrene block is lower when the surface is annealed at 120° C. or 150° C. compared to 60° C. Second, the intensity of the C—F σ* resonance increases with annealing. This result is an indication of a preferential segregation of the amphiphilic block to the air-polymer interface and suggests that the amphiphilic block is of a lower surface energy compared to polystyrene, in spite of the presence of the higher energy PEG moieties. This can be attributed to the diblock nature of the side chains and the tendency of the fluoroalkyl groups to be selectively present at the air-polymer interface. The low surface-energy fluoroalkyl groups seem to compensate for the higher surface-energy PEG moities. XPS spectra of these surfaces, discussed below, also confirmed the NEXAFS results.

Variation of surface composition with depth. NEXAFS spectroscopy indicated a preferential segregation of the amphiphilic block to the air-polymer interface, an observation consistent with expectations from a mixture of molecules with significantly different surface energies. Polystyrene has a surface energy of 39.3 mJ/m², and poly(ethylene oxide) has a higher surface energy of 43 mJ/m². A surface completely covered by fluoroalkyl groups shows surface-energy as low as 8 mJ/m². The surface segregation of the amphiphilic block should result in a depth-dependent concentration profile, which was investigated using two techniques: angle resolved XPS, and depth profiling using NEXAFS.

Figure 5:
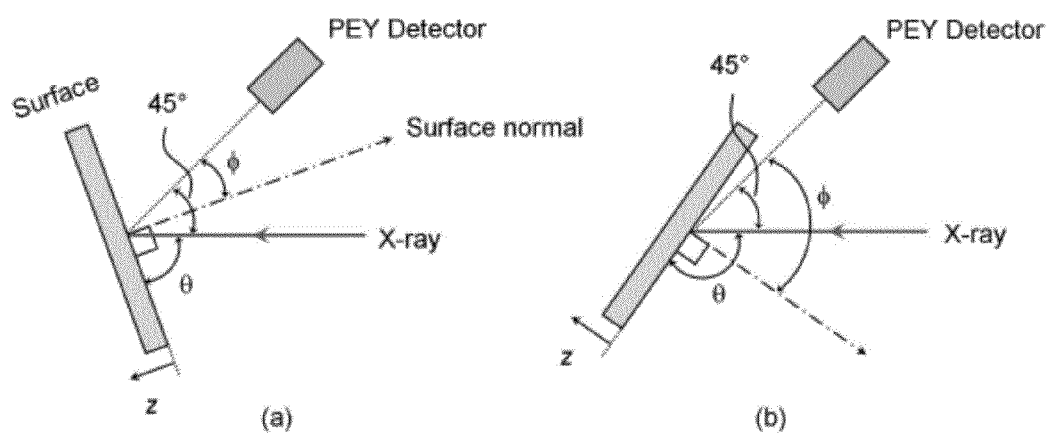
FIG. 5 illustrates the experimental arrangement for NEXAFS depth profiling experiments (top view). The electron emission angle, φ, is varied by rotating the surface about an axis normal to the plane of the paper as shown in the two different configurations (a) and (b). The angle between the path of the incident X-ray photons and the emitted Auger electrons is fixed, and is about 45°.

FIG. 5 shows the XPS spectra of the block copolymer film coated on silicon, obtained at two different electron emission angles, φ. The electron emission angle, φ, is the angle between the surface-normal and the path taken by the electrons toward the detector. The sampling depth, d, is approximately $\lambda \cos \phi$, where $\lambda$ is the inelastic mean free path (IMFP). The electron IMFP for the polymer with structure shown in FIG. 10 can be estimated, using quantitative structure-property approach of Cumpson (*Surface and Interface Analysis* 2001, 31, 23-34) based on the zeroth-order valence connectivity indices of Kier-Hall, to be:

$$\lambda^{1keV} = \left[\frac{31.17 \cdot \{4.671m + (4.393 + 1.822x + 2.512y) \cdot n\} + 4.207m}{8m + (8 + 3x + 6y) \cdot n} + 11.04\right] \overset{\circ}{A} \quad (1)$$

where the superscript 1 keV indicates that the estimated IMFP is for electrons with an energy of 1 keV.

Figure 3:
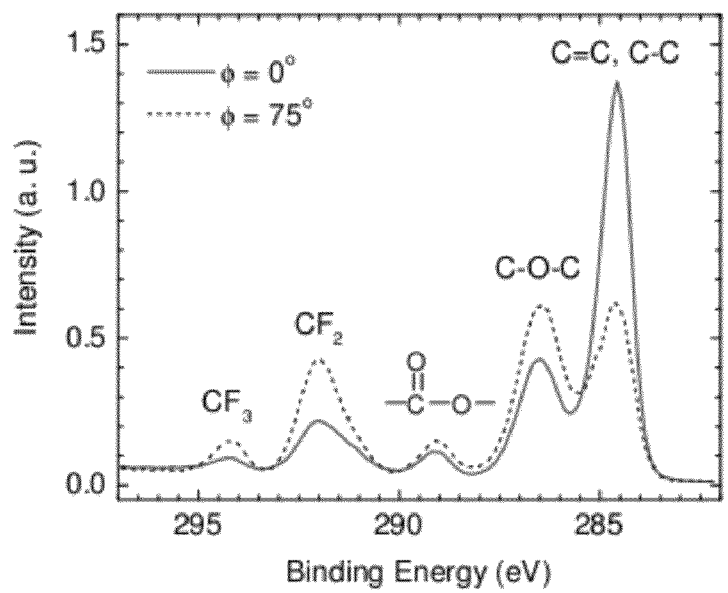
FIG. 3 illustrates an XPS spectra, at two different emission angles, of the amphiphilic block copolymer spin-coated on silicon and annealed at 120° C. for 12 hours; emission angle, φ, is the angle made by the surface-normal with the escape-path of electrons emitted by the surface.

Equation (1) assumes a statistically homogeneous mixture of the two monomers in the block copolymer thin film, despite the block architecture of the copolymer and the experimentally observed fact that there is segregation of the amphiphilic block to the surface (cf. FIG. 3). However, the $\lambda^1_{keV}$ values for the PS and the amphiphilic blocks (calculated separately) were 29.8 Å and 26.8 Å (for x=4, y=3), respectively, and within about ±11% of each other, making eq (1) a reasonable approximation for IMFP of electrons emitted by the block copolymer. The IMFP for an electron with energy E (keV) can be obtained using:

$$\lambda = \lambda^{1\ keV} \cdot (E/\text{keV})^{0.79} \quad (2)$$

See Kikuma and Tonner, *Journal of Electron Spectroscopy and Related Phenomena* 1996, 82, 53-60. The excitation energies reported by Kikuma should be adjusted by 0.6 eV for comparison with the values presented herein. The $\pi^*$ C=C resonance has been calibrated to 284.9 eV in this Example 2.

Thus, the inelastic mean free path for a C is electron with a binding energy of 294 eV, and hence a kinetic energy of 1192.6 eV, is about 3.2 nm. The electrons originating from $CF_3$ have the lowest kinetic energy in the C1s spectrum of the amphiphilic polymer surface. These electrons have a higher probability of losing energy due to inelastic processes. More than 63% of the photoelectrons originating from depths below $\lambda$ (3.2 nm) would have lost energy by inelastic scattering. These inelastically scattered electrons will not contribute to peak-intensities of our interest. In other words, most of the electrons detected are from within a depth of $\lambda$ below the surface. The sampling depth using an emission angle of 75° will be 25.8% of that using 0° emission, making the XPS results at this angle sensitive primarily to the chemical bonding within about 1 nm of the surface.

It is understood from FIG. 3 that the peak at 284.6 eV due in part to polystyrene decreases and the peaks corresponding to the amphiphilic side chains, at about 294 eV from —$CF_3$, 292 eV from —$CF_2$— and 286.6 eV from —$CH_2CH_2O$—, increase as the sampling depth is decreased. This indicates the presence of a thin layer of ethoxylated fluoroalkyl groups at the surface as well as a higher concentration of C atoms not bonded to F or O in a layer below the surface. Logically, this sub-surface layer contains phenyl rings from PS that XPS cannot distinguish from the C atoms in the polymer backbone.

Figure 4:
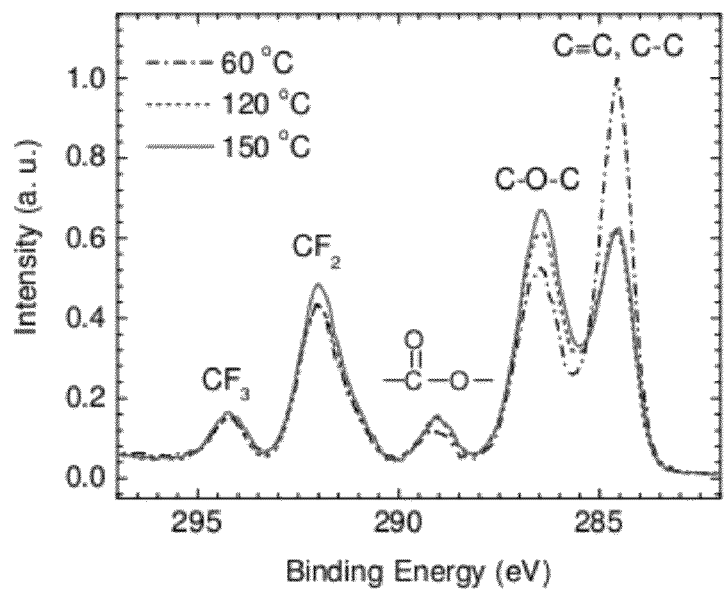
FIG. 4 illustrates XPS spectra of surfaces prepared by spin-coating a 3% (w/v) solution of the block copolymer of Example 1 in chloroform and (a) vacuum-drying at 60° C. for 12 hours, followed by (b) annealing at 120° C. for 12 hours, and (c) annealing at 150° C. for 12 hours; obtained at an electron emission angle of 75°.

FIG. 4 shows the XPS spectra of surfaces annealed at 60° C., 120° C. and 150° C., determined using an electron take-off angle of 75°. The results show a progressive depletion of C atoms not bonded to F or O, and enrichment of —$CF_2$—, —$CH_2CH_2O$— and —COO— carbon atoms of the amphiphilic side chains as the annealing temperature is increased. This is evident from the intensity of the peaks at 284.6 eV and 286.6 eV, associated with C=C carbon atoms of styrene and —$CH_2CH_2O$— carbon atoms of PEG, respectively, and is consistent with inferences from NEXAFS spectroscopy (cf. FIG. 2). Surface-reconstruction occurs on annealing where the thin-layer of amphiphilic side chains is further enriched in the fluoroalkyl and PEG components, possibly by migration of the higher surface-energy PS block toward the bulk.

Depth Profiling Using NEXAFS Spectroscopy. While XPS is not capable of separating C atoms in polystyrene phenyl rings from C atoms in the polymer backbone, NEXAFS spectroscopy can directly monitor the former from the sharp $1s \rightarrow \pi^*_{C=C}$ resonance at about 285.5 eV. Depth profiling using NEXAFS peaks can be accomplished by two methods. The first method is based on making the entrance grid bias (EGB) of the channeltron photoelectron detector progressively more negative so that only Auger electrons originating from increasing thinner sample depths, and carrying information about the molecular composition of the film could be detected (see Genzer et al. *J. Appl. Phys.* 2002, 92, 7070-7079). The second method involves obtaining the NEXAFS spectra at different electron emission angles by rotation of the sample (about a vertical axis), relative to the "in-plane" partial electron yield (PEY) detector (Fischer et al. *Rev. Sci. Instrum.* 1989, 60, 1596), as shown in FIG. 5. Results from the second method will be described below.

Figure 6:
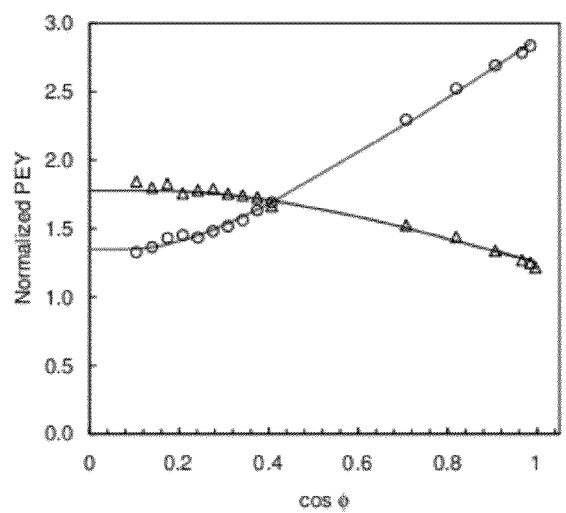
FIG. 6 illustrates the experimental dependence of the PEY corresponding to 1s → $\pi^*_{C=C}$ resonance (○) and 1s → $\sigma^*_{C-F}$ resonance (△) with the cosine of the electron emission angle, φ. The $\pi^*_{C=C}$ peak is associated with the phenyl ring C atoms while the $\sigma^*_{C-F}$ signal arises from the C atoms bonded to F. The curves are theoretical fits assuming a model shown in eq (7).

FIG. 6 shows the experimental variation in the normalized partial electron yields at 285.5 eV and 293.0 eV, corresponding to transitions to $\pi^*_{C=C}$ and $\sigma^*_{C-F}$ orbitals, respectively, with the cosine of the emission angle, $\phi$. As discussed above, the probe-depth, d, at an emission angle, $\phi$, is proportional to $\lambda \cos \phi$, thus making the abscissa of FIG. 6 directly proportional to the probe depth. The smooth curves were obtained by fitting the experimental data with eq (3), which translates to the concentration profile f(z) given in eq (4).

Equation (3) was derived by first assuming a concentration profile, f(z) [eq (4)], and then using the equation relating the normalized PEY to the concentration profile of the phenyl ring C atoms [eq(7) discussed in Appendix]. In eqs (3) and (4), $I_a$ is the normalized PEY of the $\pi^*_{C=C}$ resonance, $\sigma_x(hv)$ is the X-ray absorption cross-section, z is the depth below the surface of the polymer film, and f(z) is the fraction of the total number of C atoms at depth z that belong to the phenyl ring. The parameters b, m and a of the model for f(z) are positive numbers. It is seen that except at high electron emission angles (low values of cos $\phi$), the assumed concentration profile fits the experimental data fairly well.

$$I_a = \frac{\sigma_x(285.5\ \text{eV})}{\sigma_x(320.0\ \text{eV})}\left\{b \pm m\lambda \cdot \cos\phi \cdot \exp\left(-\frac{a}{\lambda\cos\phi}\right)\right\} \quad (3)$$

$$f(z) = \begin{cases} b & 0 \le z \le a \\ b + m(z-a) & z > a \end{cases} \quad (4)$$

Figure 7:
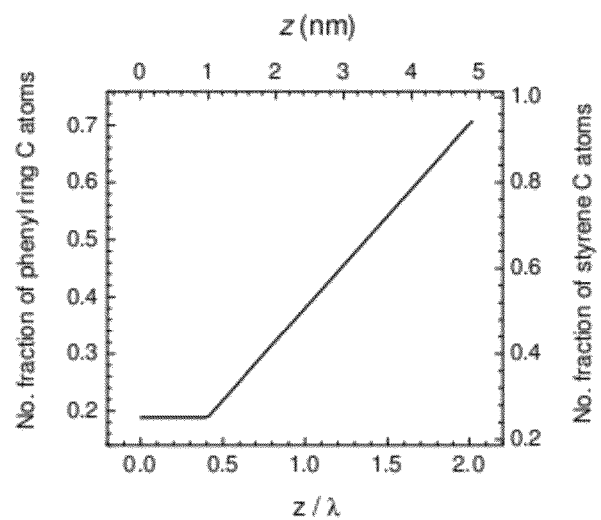
FIG. 7 illustrates variation of phenyl ring composition with depth z. The number fraction of carbon atoms in phenyl rings is equal to the number fraction of C atoms in polystyrene multiplied by 0.75. The top axis shows depth z normalized using an electron attenuation length[53], λ, of 2.43 nm.

FIG. 7 shows the fraction of the C atoms that belong to the phenyl ring, at different depths, z (non-dimensionalized using $\lambda$), below the surface. It is apparent that polystyrene concentration is lower at the surface, shows little or no variation up to $z/\lambda$ of about 0.4, and then increases deeper into the film. The actual depths, calculated using the value of 2.43 nm for $\lambda$, are also shown in FIG. 7. In conjunction with results from angle-resolved XPS, one can conclude that the thin layer at the surface with a thickness of about 1.0 nm (corresponding to $z/\lambda=0.4$), which is depleted in polystyrene, is occupied by the ethoxylated fluoroalkyl side chains in concentrations much higher than the average composition in bulk.

In summary, XPS and NEXAFS results indicated the presence of the amphiphilic ethoxylated fluoroalkyl groups at the air-polymer interface. On immersing the surface in water, surface reconstruction occurred where the poly(ethylene glycol) parts of the ethoxylated fluoroalkyl side chains are exposed at the water-polymer interface. This is supported by water contact angle measurements for the surface in air, where the higher advancing water contact angle can be attributed to the presence of hydrophobic fluoroalkyl groups at the surface and the lower receding angle to the presence of hydrophilic PEG.

Contact angle measurements also suggested that surface reconstruction upon immersion in water occurred by two different mechanisms. The faster process is possibly due to reorientation of the side-chains as shown in FIG. 10, while the slower process is that of diffusion of the polystyrene block toward the interior of the polymer coating and the surface-active block toward the polymer-water interface. The thermodynamically favored surface composition is expected to be the one that is rich in PEG groups. The associated minimization of polymer-water interfacial energy is expected to lower the driving force for adsorption of biomacromolecules at the surface.

Surface Morphology. Scanning Force Microscopy of the spray-coated surfaces indicated a relatively uncomplicated surface morphology (cf. Gudipati et al. *J. Polym. Sci. Part A: Polym. Chem.* 2004, 42, 6193-6208), and complete coverage of the underlying SEBS layer. The spray-coated surfaces used for the biofouling assays, had a surface roughness of about 0.9 μm (determined over an area of about 0.6 mm×0.8 mm) Spin-coated surfaces used for NEXAFS and XPS studies showed less than 3 nm surface roughness over 0.6 mm×0.8 mm regions.

Figure 8:
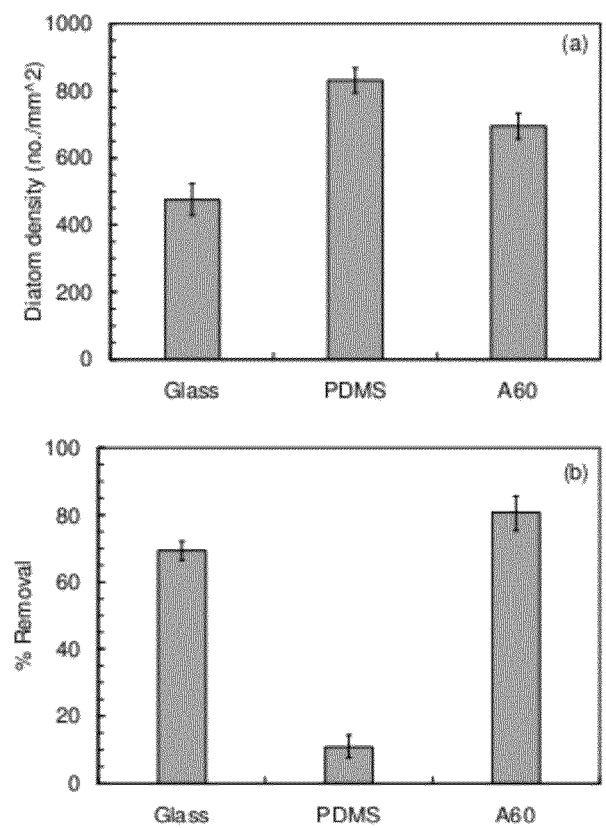
FIG. 8 illustrates (a) settlement and (b) percent removal of *Navicula* on glass, PDMS and amphiphilic polymer surfaces. Each point represents the mean percentage removal from 90 counts from 3 replicate slides. Bars represent 95% confidence limits derived from arcsine transformed data. A60 denotes the amphiphilic polymer surfaces annealed at 60° C.

Marine antifouling properties. Attachment of diatoms. The settlement densities of *Navicula* on glass, PDMS and amphiphilic surfaces are shown in FIG. 8(*a*). Because the settlement of *Navicula* is by gravity, one would expect the same settlement density on all three surfaces. However, there were more cells adhered to the PDMS than to the glass standard surfaces, which probably reflects the weak attachment strength of *Navicula* to glass and the detachment of some cells at the gentle washing stage. This is confirmed from the data in FIG. 8(*b*) where the settled cells were exposed to 53 Pa wall shear stress in a turbulent flow channel, and the percentages of removed cells are compared. The attachment strength was the lowest on the amphiphilic surface with (81±5) % removal, compared to (69±3) % from glass, and (11±4) % from PDMS.

Figure 9:
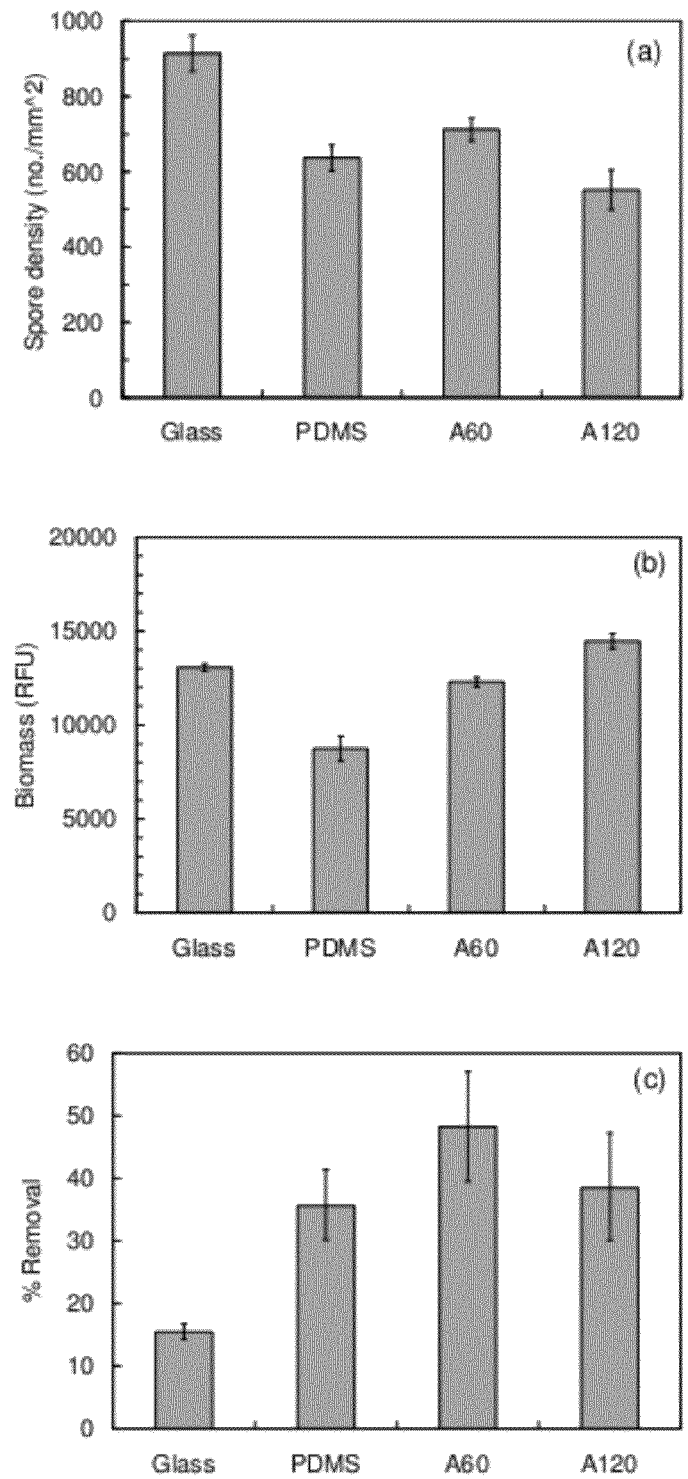
FIG. 9 illustrates the settlement of *Ulva* spores on amphiphilic surfaces. Bars show 95% confidence limits from 90 counts, 30 on each of 3 replicate slides. (b) The growth of *Ulva* sporelings on amphiphilic surfaces after 7 days. Each point is the mean biomass from 6 replicate slides measured using a fluorescent plate reader (RFU; relative fluorescence unit). Bars show standard error of the mean. (c) The percentage removal of *Ulva* sporelings from amphiphilic surfaces after exposure to shear stress of 53 Pa in water channel. Each point is the mean biomass from 6 replicate slides. Bars show standard error of the mean derived from arcsine transformed data. A60 and A120 are the amphiphilic surfaces annealed at 60° C. and 120° C., respectively.

Settlement of *Ulva* zoospores. Amphiphilic surfaces annealed at 60° C. and 120° C. were tested. The settlement density of spores was broadly similar on both of the amphiphilic surfaces and on the PDMS coatings (cf. FIG. 9*a*). The settlement density on glass was higher.

Growth of sporelings. Sporeling growth was also similar on all surfaces (cf. FIG. 9*b*). There were no signs of toxicity from any of the surfaces.

Strength of attachment of sporelings. Removal of sporelings (cf. FIG. 9*c*) from both amphiphilic surfaces was not statistically different to that from the PDMS standard, but removal from all three surfaces was significantly higher than from glass ($F_{3,20}$=7.18 P<0.05). It is likely that H-bonding or electrostatic interactions with glass caused stronger adhesion (see Roth et al. *J. Colloid Interface Sci.* 1998, 203, 218-221). In a different experiment, the 60° C. annealed surfaces were treated with spore suspensions of different concentrations and the settled spores were cultured over a period of 8 days to form biofilms of sporelings.

Sporeling removal was found to be greatest from surfaces that were exposed to the most concentrated spore suspension (and hence developed the highest sporeling density). Observations indicated that while there was almost complete removal from the amphiphilic surface, a large percentage of the sporelings remained on the glass surface even after exposure to water flow. Removal of sporelings from the amphiphilic surfaces seemed to be due to the entry of water between the sporeling biofilm and the coating. In other words, the sporelings were more strongly attached to each other than to the coating, and the biofilm detached in sheets.

As discussed above, XPS and NEXAFS spectroscopy showed that the surface annealed at 120° C. had a lower content of polystyrene and a higher content of amphiphilic side-chains than the surface annealed at 60° C. However, the annealing temperature did not have a statistically significant effect on the release of sporelings. Based on the results of the captive air-bubble contact-angle study, it seems that both the surfaces (A60 and A120 in FIG. 9) undergo surface reconstruction under water to result in surfaces predominantly covered by PEG, with the fluoroalkyl and styrene groups buried below. Thus, annealing did not have a significant effect on the adhesion strength of sporelings possibly because of similar molecular compositions and orientations at the polymer-water interface.

Conclusion. Surfaces of the comb-like block copolymers with ethoxylated fluoroalkyl side chains are unique as they showed high removal of both *Ulva* and *Navicula*. The PDMS surfaces resulted in high release of *Ulva* sporelings, compared to low release of diatom cells. The high removal of *Navicula* from the amphiphilic surface can be explained based on the fact that the surface reconstructs to become as hydrophilic as a PEGylated surface when immersed in water, and that *Navicula* adheres weakly to hydrophilic surfaces.

The settlement of *Ulva* spores on the amphiphilic surfaces is similar to that on PDMS. Similarly, the strength of attachment of *Ulva* sporelings to the amphiphilic surfaces and PDMS are comparable. This indicates that the surface may become hydrophobic by exposing the fluoroalkyl groups when in contact with *Ulva*. However, entrance of water in between the *Ulva* biofilm and the coating surface suggests that the surface retained its hydrophilic character even after contact with the spore adhesive.

Ingress of water between the coating and the biofilm was a distinctive property of the amphiphilic surfaces, and was not observed in the case of PDMS or glass. It is likely that the chemical ambiguity of the amphiphilic surface lowers the entropic and enthalpic driving forces for adsorption of adhesive macromolecules, and hence the adhesion strength of the whole cell.

Example 3

Preparation of Surface-Active Block Copolymers Containing Ester, Amide and Amine Linkages The following procedures can be used to prepare various polymers of the invention.

Part 1. Synthesis of Functional Carboxylic Acid and Attachment to Hydroxyl Containing Polymers.

Groups represented by R—OH, where R is an alkyl, fluoroalkyl, semifluorinated alkyl, ethoxylated fluoroalkyl (Zonyl) or a PEG group, can be oxidized as described by Krishnan et al. (*Biomacromolecules* 2006, 7, 1449-1462). For example, the terminal alcohol group can be converted to a carboxyl group by the following techniques.

Synthesis of carboxyl-terminated groups from hydroxyl-terminated groups. Relatively mild oxidizing conditions were developed because of reports that strong oxidizing agents, e.g. permanganate, cause polyether chain degradation (Li et al. *Biomacromolecules* 2003, 4, 1055-1067). Oxidation of primary alcohols to carboxylic acid using N-oxoammonium salt is a highly attractive, mild, and metal-free route that has been extensively studied (Bobbitt et al. *J. Org. Chem.* 1998, 63, 9367-9374). The N-oxoammonium salt is usually generated in situ by using a catalytic amount of 2,2,6,6-tetramethylpiperidine-1-oxy radical (TEMPO) and a stoichiometric amount of an oxidant such as bleach (NaOCl) or trichloroisocyanuric acid (TCCA). The N-oxoammonium ion produced by the reaction of TEMPO with TCCA oxidizes the hydroxymethyl group of the hydroxyl-terminated group to an aldehyde, which is further oxidized to a carboxylic acid by the hypochlorite ion generated by NaBr-catalyzed hydrolysis of TCCA.

For example, mPEG was converted to a carboxyl-terminated mPEG by the following procedure. One hundred mL of saturated sodium bicarbonate solution (10.3% w/v, 1.23 M) was added to a solution of 16.5 g (30 mmol) of mPEG in 150 mL acetone. After cooling to 0° C., 0.617 g (3 mmol) of NaBr and 0.312 g (2 mmol) TEMPO were added, followed by a slow addition of 16.269 g (70 mmol) of TCCA. The reaction mixture was warmed to room temperature and stirred for about 24 hours at room temperature, after which 10 mL of 2-propanol was added. After the stirring was stopped, a fine white solid settled down. The supernatant was decanted, mixed with Celite 545 filter aid (diatomaceous earth), and filtered. The clear, yellow filtrate was concentrated under vacuum to remove acetone and treated with 100 mL of 1 M $Na_2CO_3$ in water (10.6% w/v). This resulted in further precipitation of a white solid, and a clear, colorless filtrate after filtration.

The precipitate, consisting of isocyanuric acid, its tautomer, cyanuric acid, and their derivatives, was insoluble in chloroform. The aqueous phase was washed with ethyl acetate, acidified using 150 mL of 2 N HCl solution to convert the water-soluble mPEG carboxylate to mPEG carboxylic acid that could be extracted with chloroform. Solvent was evaporated from the chloroform solution to yield 15.5 g of viscous, colorless liquid after drying under vacuum (ca. 91.6% yield). Quantitative conversion was confirmed by the disappearance of the δ 2.9 signal in $^1$H NMR, and also disappearance of δ 61.3 and δ 72.2 signals and appearance of δ 171.8 signal in $^{13}$C NMR.

This procedure can be used to prepare carboxyl-terminated side chains from the various hydroxyl-terminated groups described herein, as illustrated in Scheme 2.

Scheme 2.

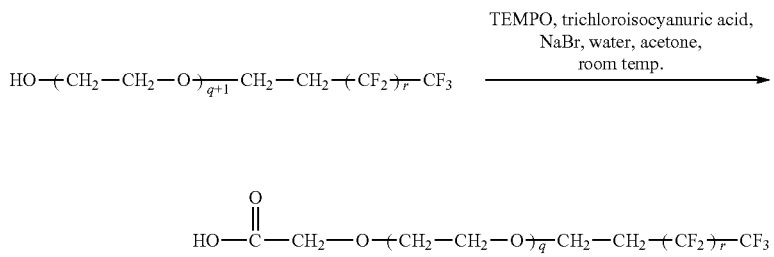

Vinyl containing polymers can be hydroxylated by the hydroboration/oxidation technique (see Krishnan, ibid., for the reaction scheme and references). The hydroxylated polymer can be reacted with functional carboxylic acids to form a surface-active polymer with ester linkages. The ethoxylated fluoroalkyl group $Z = -(CH_2CH_2O)_qCH_2CH_2(CF_2)_rCF_3$ can be attached to the polymer backbone via an oxyacetoxy group, $-O-CH_2-C(=O)-O-$ as illustrated in Scheme 3.

Scheme 3.

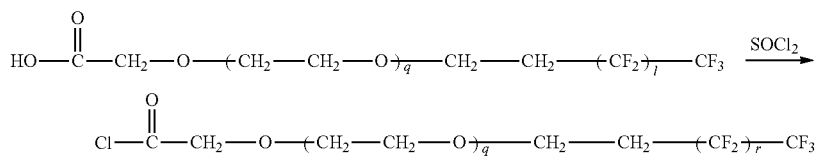

-continued

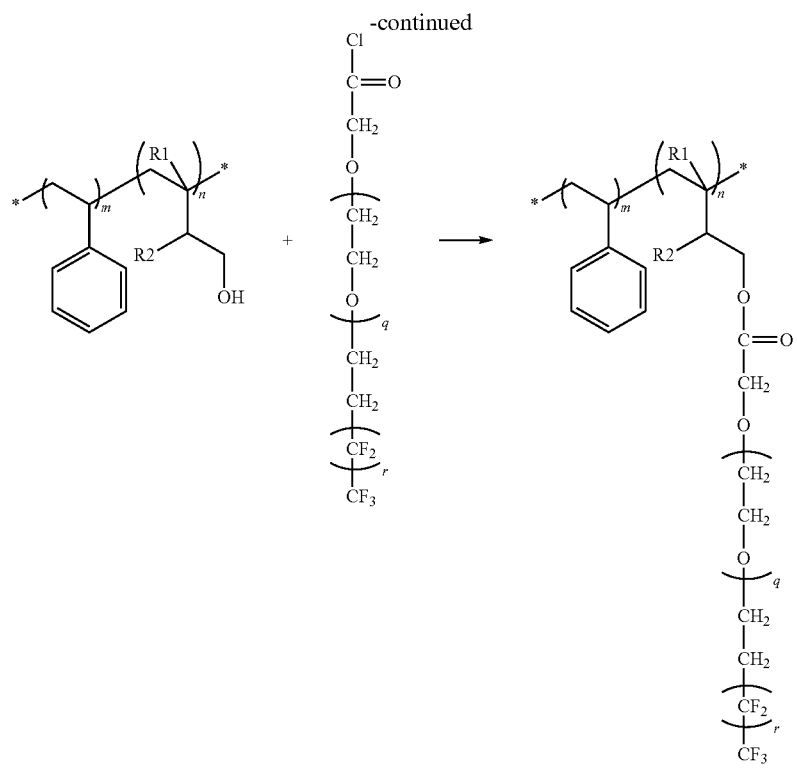

R1, R2 = H (or CH₃)

Part 2. Synthesis of Amino Polymers and Attachment of Functional Carboxylic Acids.

Vinyl containing polymers can be hydroxylated by a hydroboration/oxidation technique (see Krishnan, ibid., for the reaction scheme). See for example, polymers of formula I. Bromination of the hydroxyl groups can be achieved as described in Youngblood et al. (*Biofouling* 2003, 19 (Supplement), 91-98). Amino groups can be introduced in the brominated polymer using reaction with NaN₃ followed by LiAlH₄ reduction. Functional carboxylic acids, which are prepared as shown in Scheme 2, can be reacted with the aminated polymer to form surface-active polymers with oxyacetamide, —O—CH₂—C(═O)—NH—, linkages, as illustrated in Scheme 4.

Scheme 4.

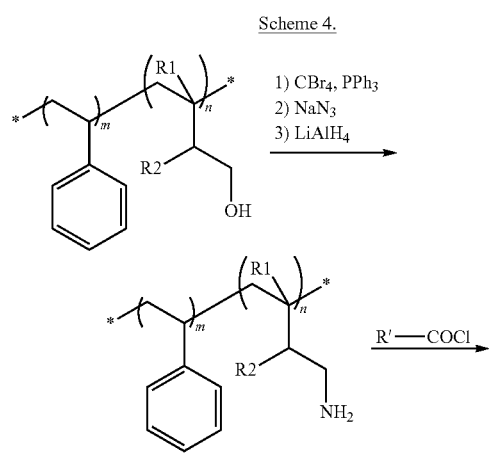

R1 = H (or CH₃), R2 = H (or CH₃)
R' = alkyl, perfluoroalkyl, semifluorinated alkyl, ethoxylated fluoroalkyl (Zonyl) or PEG Part 3. Epoxide Ring Opening and Formation of Amine Linkages.

Polymers containing vinyl groups can be epoxidized as discussed in Ober et al. (U.S. Patent Application Publication No. 2006/0083854). The epoxidized polymers can be reacted with functional amines prepared as shown in Scheme 5 to obtain polymers with secondary amine linkages and hydroxyl groups. The hydroxyl groups can be further attached to functional side chains via ester, ether or amine linkages.

Scheme 5.

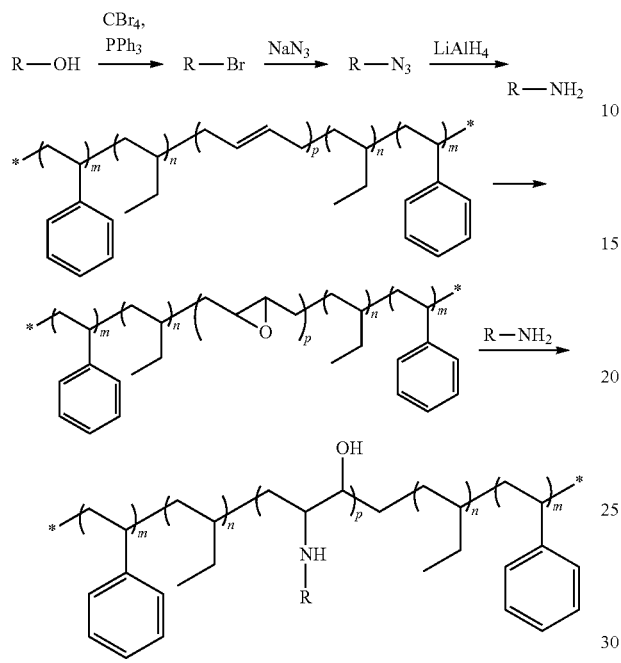

R = alkyl, perfluoroalkyl, semifluorinated alkyl, ethoxylated fluoroalkyl (Zonyl) or PEG The penta-block precursor shown in Scheme 5 can be obtained by anionic polymerization using a dilithium initiator (see Matmour et al. *J. Am. Chem. Soc.* 2006, 128, 8158-8159, and the references therein). Polymerization of butadiene in a non-polar solvent such as cyclohexane will result in predominantly 1,4-polybutadiene. Further addition of butadiene in the presence of a polar-modifying agent such as 1,2-dipiperidinoethane will generate polybutadiene blocks with high vinyl contents (Halasa, et al. *J. Polym. Sci., Polym. Chem. Ed.* 1981, 19, 1357-1360).

A final addition of styrene and deactivation of the living chain ends with methanol will give a penta-block copolymer with a 1,4-polybutadiene central block attached to 1,2-polybutadiene-block-polystyrene on either ends. Selective hydrogenation of the $CH_2=CH-$ (vinyl) groups (see Escobar Barrios et al. *Eur. Polym. J.* 2003, 39, 1151-1167, and Ko et al. *Eur. Pat. Appl.* 2001: EP 2000-401970 20000707) will produce the precursor shown in Scheme 5.

Part 4. Side Chain Attachment by Alkylation of Amines.

Polymers with amino side chains, which can be prepared as shown in Scheme 4, can be alkylated using a functional alkyl halide in the presence of a base to form amine linkages as shown in Scheme 6.

Scheme 6.

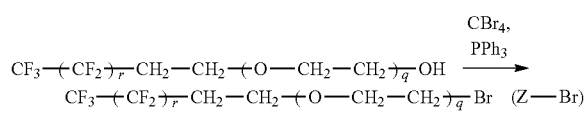

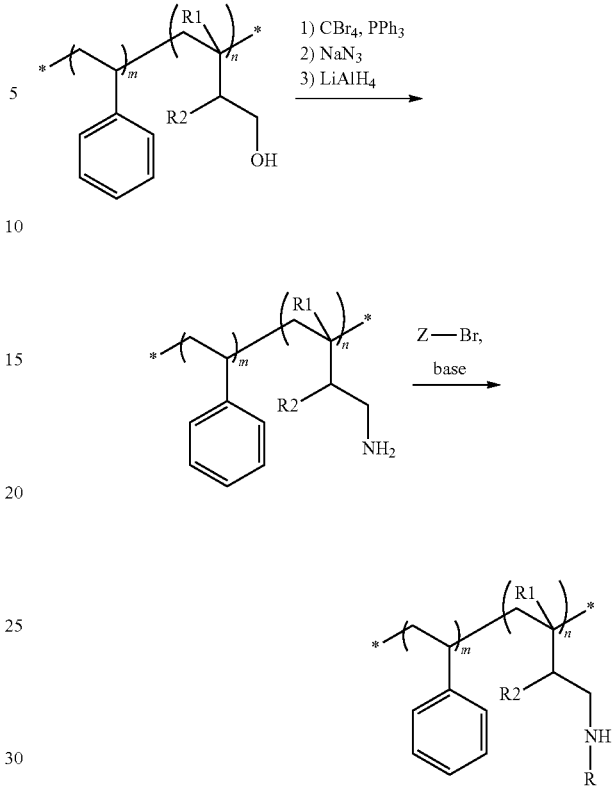

R1 = H (or $CH_3$), R2 = H (or $CH_3$)

R = alkyl, perfluoroalkyl, semifluorinated alkyl, ethoxylated fluoroalkyl (Zonyl) or PEG Part 5. Synthesis and Polymerization of Functional Acrylates.

Groups represented by R—OH, where R is an alkyl, fluoroalkyl, semifluorinated alkyl, ethoxylated fluoroalkyl (Zonyl) or a PEG group, can be reacted with acryloyl chloride to obtain an acrylate, which can be further polymerized. See for example, polymers of formula II and the polymers and techniques described by Krishnan et al. *Langmuir* 2006, 22, 5075-5086. Block copolymers or random copolymers can be obtained by controlled free radical polymerization techniques (ATRP, RAFT, nitroxide mediated polymerization, etc.). The ethoxylated fluoroalkyl group $Z=-(CH_2CH_2O)_qCH_2CH_2(CF_2)_rCF_3$ can be attached to the polymer backbone via the ester group, $-C(=O)-O-$, as illustrated in Scheme 7.

Scheme 7.

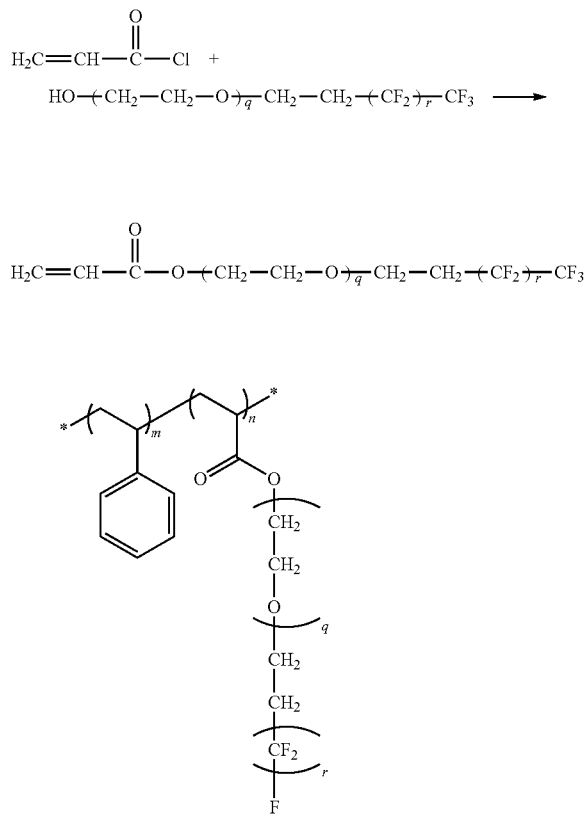

Part 6. Synthesis of Functional Amines and Attachment to Carboxyl Containing Polymers.

Groups represented by R—OH, where R is an alkyl, fluoroalkyl, semifluorinated alkyl, etc., can be converted to amines as shown below in Scheme 8. See for example, polymers of formula II. Acrylic or methacrylic acid containing polymers can be reacted with the functional amines to obtain surface-active polymers with amide linkages.

Scheme 8.

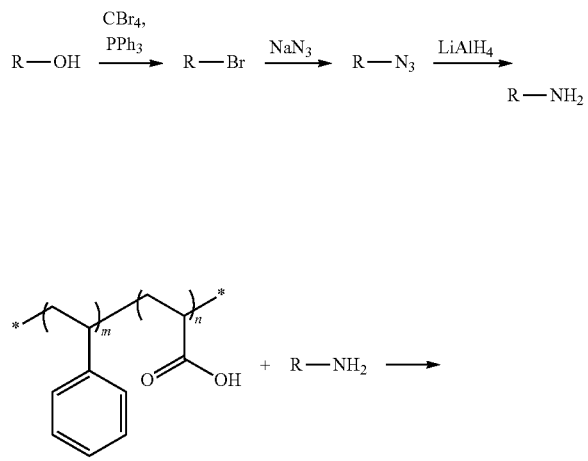

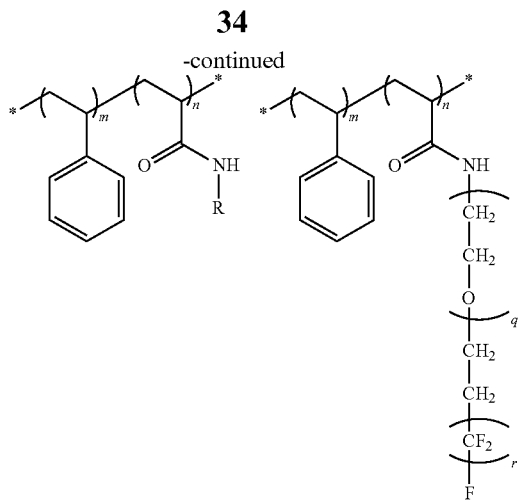

R = alkyl, perfluoroalkyl, semifluorinated alkyl, ethoxylated fluoroalkyl (Zonyl) or PEG Each of the polymers described in this Example can be random copolymers, or block copolymers with two or more blocks.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A polymer comprising formula (II):

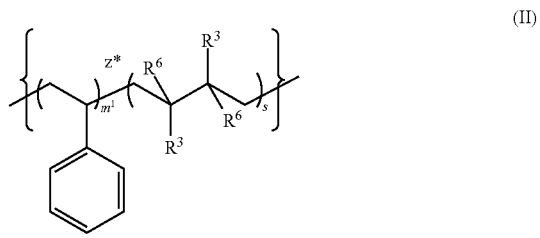

wherein $m^1$ is about 5 to about 2000;
s is about 5 to about 2000;
each $R^6$ is independently H or alkyl, provided that when one $R^6$ of any given subunit s is alkyl, the other $R^6$ of the same subunit s is H;
each $R^3$ is independently H, OH, halo, carboxy, or alkyl wherein alkyl is optionally at least partially fluorinated; alkyl-terminated (-ethylene glycol-)$_n$ wherein n is about 2 to about 24; wherein each alkyl or alkyl-terminated (-ethylene glycol-)$_n$ is covalently bonded to the carbon of $R^3$ through an ester, amide, or amino group; or a moiety of formula Z:

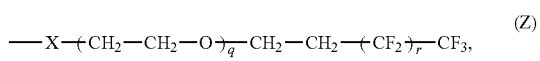

wherein each X is independently —C(=O)—O— or —C(=O)—NH—, linking the moiety of formula Z to the carbon attached to $R^3$, each q is independently 1 to about 25, and each r is independently 1 to about 18;

provided that when one $R^3$ of any given subunit s is a moiety of formula Z, the other $R^3$ of the same subunit s is not a moiety of formula Z;

provided that at least one $R^3$ of formula II is a moiety of formula Z; and the dispersement of each individual s subunit and each individual $m^1$ subunit on either side of z* is random and each individual s subunit and each individual $m^1$ subunit occurs interchangeably with any other s or $m^1$ subunit within the brackets of formula II.

2. The polymer of claim 1 wherein each X is —C(=O)—O—, q is 1 to about 15, and r is 1 to about 8.

3. The polymer of claim 1 wherein the molecular weight of the polymer is about 5 kDa to about 2,000 kDa.

4. The polymer of claim 1 wherein the polymer exhibits antifouling properties toward one or more of marine algae, algal spores, bacterial cells, diatoms, and protozoa.

5. An antifouling surface that includes a surface coating comprising the polymer of claim 1 and optionally a base layer that comprises an elastomeric polymer.

6. The antifouling surface of claim 5, wherein the base layer is present.

7. The polymer of claim 1 wherein each q is 1 to about 15 and each r is 1 to about 8.

8. The polymer of claim 1 wherein each X is —C(=O)—O—.

* * * * *